United States Patent
Zhang

(10) Patent No.: US 6,541,608 B1
(45) Date of Patent: Apr. 1, 2003

(54) T CELL RECEPTOR Vβ-Dβ-Jβ SEQUENCE AND METHODS FOR ITS DETECTION

(75) Inventor: Jingwu Z. Zhang, Missouri City, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/641,576

(22) Filed: Aug. 18, 2000

Related U.S. Application Data

(63) Continuation-in-part of application No. 09/507,819, filed on Feb. 22, 2000, now Pat. No. 6,303,314.
(60) Provisional application No. 60/121,311, filed on Feb. 23, 1999.

(51) Int. Cl.[7] ......................... C07K 14/00; C07H 21/02; C07H 21/04
(52) U.S. Cl. ...................... 530/350; 536/23.1; 536/24.3
(58) Field of Search ......................... 530/350; 536/23.1, 536/24.3

(56) References Cited

U.S. PATENT DOCUMENTS

| | | | |
|---|---|---|---|
| 5,198,537 A | 3/1993 | Huber et al. | ................. 530/406 |
| 5,614,192 A | 3/1997 | Vandenbark | ............. 424/185.1 |
| 5,667,967 A | * 9/1997 | Steinman et al. | |

FOREIGN PATENT DOCUMENTS

| | | |
|---|---|---|
| WO | WO 93/12814 | 7/1993 |
| WO | WO 95/34320 | 12/1995 |

OTHER PUBLICATIONS

Gold, D. P. et al., "Results of a phase I clinical trial of a T–cell receptor vaccine in patients with multiple sclerosis. II. Comparative analysis of TCR utilization in CSF T–cell populations before and after vaccination with a TCRVβ6 CSF T–cell populations before and after vaccination with a TCRVβ6 CDR2 peptide.", *Journal of Neuroimmunology* 76:29–38 (1997).

Goldrath, A. W. et al., "Differences in Adhesion Markers, Activation Markers, and TcR in Islet Infiltrating vs. Peripheral Lymphocytes in the NOD Mouse", *Journal of Autoimmunity* 8:209–220 (1995).

Lider, O. et al., "Anti–Idiotypic Network Induced by T Cell Vaccination Against Experimental Autoimmune Encephalomyelitis", *Science* 239:181–184 (1988).

Lund, F. E. et al., "CD38: a new paradigm in lymphocyte activation and signal transduction", *Immunological Reviews* 161:79–93 (1998).

Medaer, R. et al., "Depletion of myelin–basic–protein autoreactive T cells by T–cell vaccination; pilot trial in multiple sclerosis", *The Lancet* 346:807–8 (1995).

Sakaguchi, S. et al., "T Cell–Mediated Maintenance of Natural Self–Tolerance: its Breakdown as a Possible Cause of Various Autoimmune Diseases", *Journal of Autoimmunity* 9:211–220 (1996).

Van Gool, S. W. et al., "CD80, CD86 and CD40 Provide Accessory Signals in a Multiple–Step T–Cell Activation Model", *Immunological Reviews* 153:47–83 (1996).

Van de Stolpe, A. et al., "Intercellular adhesion molecult–1", *J. Mol. Med.* 74:13–33 (1996).

Wilson, D. B. et al., "Results of a phase I clinical trial of a T–cell receptor peptide vaccine in patients with multiple sclerosis. I. Analysis of T–cell receptor utilization in CSF cell populations", *Journal of Neuroimmunology* 76:15–28 (1997).

Zhang, J. et al., "In Vivo Clonotypic Regulation of Human Myelin Basic Protein–Reactive T Cells by T Cell Vaccination", *Journal of Immunology* 155:5868–77 (1995).

Zhang, J. et al., "MHC–Restricted Depletion of Human Myelin Basic Protein–Reactive T Cells by T Cell Vaccination", *Science* 261:1451–54 (1993).

International Search Report for International application No. PCT US00/40006 (Mailed Jun. 12, 2000).

Boehringer Mannheim Corporation. Boehringer Mannheim Biochemicals 1993 Catalog, p. 87.

Hong, J. et al., "A common TCR V–D–J Sequence in Vα13.1 T Cells Recognizing an Immunodominant Peptide of Myelin Basic Protein in Multiple Sclerosis", *Journal of Immunology* 163:3530–3538 (1999).

Kosovska, M., "T cell recognition motifs of an immunodominant peptide of myelin basic protein in patients with multiple sclerosis: structural requirements and clinical implications" *Eur. J. Immunology*, 28:1894–1901 (1998).

Zang, Y.C.Q. et al. "Restricted TCR $V_\beta$ gene rearrangements in T–Cells recognizing an immunodominant peptide of myelin basic protein in DR2 patients with multiple sclerosis" *International Immunology* 10:991–998 (1998).

(List continued on next page.)

Primary Examiner—Ethan C. Whisenant
(74) Attorney, Agent, or Firm—Katten Muchin Zavis Rosenman

(57) ABSTRACT

In one embodiment, the present invention is directed to a first oligonucleotide comprising the sequence of or derived from 5'-CTAGGGCGGGCGGGACTCACCTAC-3' or the nucleic acid sequence complementary thereto. The first oligonucleotide can be used with a nucleic acid of between 15 and 30 nucleotides that does not comprise the sequence of the first oligonucleotide and is found in the region from Vβ to Jβ of the Vβ13.1 gene in Vβ13.1 T cells, wherein the sequences of the oligonucleotide and the nucleic acid are not found on the same strand of the Vβ13.1 gene pair, to amplify a portion of the Vβ13.1 gene. Alternatively, the first oligonucleotide can be used with a labeling moiety in methods of detecting a LGRAGLTY motif found in T cell receptors of Vβ13.1 T cells. This motif is associated with autoimmune diseases, such as multiple sclerosis (MS). Once the motif is detected, the autoimmune disease can be treated or its progress monitored. The autoimmune disease can be treated by administering one or more peptides comprising the LGRAGLTY motif.

4 Claims, 7 Drawing Sheets

OTHER PUBLICATIONS

Database CAPLUS, Accession No. 1998:787586, Zhang, J., "Emerging therapeutic targets in multiple sclerosis: suppression and elimination of myelin–autoreactive T–lymphocytes," abstract, *Emerging Therapeutic Targets*, 2:137–156 (1998).

Zang, Y.C. Q, et al. "Preferential Recognition of TCR Hypervariable Regions by Human Anti–Idiotypic T Cells Induced by T Cell Vaccination" *Journal of Immunology* 164: 4011–4017 (2000).

Chou, Y.K., et al. "Immunity to TCR Peptides in Multiple Sclerosis II. T Cell Recognition of V$\beta$5.2 and V$\beta$6.1 CDR2 Peptides" *Journal of Immunology* 152: 2520–2529 (1994).

Bieganowska, K.D., et al. "Direct Ex Vivo Analysis of Activated, Fas–sensitive Autoreactive T Cells in Human Autoimmune Disease" *Journal of Experimental Medicine* 185: 1585–1594 (1997).

Wucherpfennig, K.W., et al. "Shared Human T Cell Receptor V$_\beta$ Usage to Immunodominant Regions of Myelin Basic Protein" *Science* 248: 1016–1019 (1990).

Saiki, R.K. et al. "Analysis of enzymatically amplified $\beta$–globin and HLA–DQ$\alpha$ DNA with allele–specific oligonucleotide probes" *Nature* 324:163–166 (1986).

Stratagene 1988 Product Catalog p. 39.

Vandenbark A.A. et al. "Immunization with a synthetic T–cell receptor V–region peptide protects against experimental autoimmune encephalomyelitis" *Nature* 341: 541–544 (1989).

Howell M.D. et al. "Vaccination against experimental allergic encephalomyelitis with T cell receptor peptides" *Science* 246:668–670 (1989).

Offner H. et al. "T cell receptor peptide therapy triggers autoregulation of experimental encephalomyelitis" *Science* 251:430–432 (1991).

Vandenbark A.A. et al. "Treatment of multiple sclerosis with T–cell receptor peptides: Results of a double–blind pilot trial" *Nature Medicine* 2:1109–1115 (1996).

\* cited by examiner

T cell reactivity (CPM±SD)

| Alanine substituted peptides | MS1-E2.6 | MS1-C3.1 | MS1-E3.1 |
|---|---|---|---|
| 83-ENPVVHFFKNIVTPRTP-99 | 74,189 ± 6,224 | 28,966 ± 1,100 | 31,236 ± 3,099 |
| A---------------- | 59,328 ± 2,583 | 42,446 ± 676 | 38,880 ± 1,483 |
| -A--------------- | 68,881 ± 3,155 | 33,165 ± 1,883 | 31,243 ± 1,036 |
| --A-------------- | 64,901 ± 377 | 27,019 ± 3,085 | 24,487 ± 731 |
| ---A------------- | 65,519 ± 588 | 21,340 ± 1,288 | 34,289 ± 357 |
| ----A------------ | 65,205 ± 241 | 35,032 ± 5,649 | 34,080 ± 2,274 |
| -----A----------- | 74,224 ± 526 | 16,199 ± 412 | 35,242 ± 300 |
| ------A---------- | 67,916 ± 1,979 | 34,437 ± 88 | 16,853 ± 690 |
| -------A--------- | 2,504 ± 519 | 907 ± 10 | 334 ± 38 |
| --------A-------- | 51,052 ± 4,329 | 26,400 ± 3,969 | 12,577 ± 610 |
| ---------A------- | 1,787 ± 120 | 3,364 ± 275 | 1,658 ± 78 |
| ----------A------ | 69,699 ± 3,649 | 7,649 ± 337 | 16,598 ± 440 |
| -----------A----- | 1,710 ± 34 | 35,340 ± 476 | 42,982 ± 1,605 |
| ------------A---- | 48,169 ± 1,418 | 32,109 ± 570 | 21,977 ± 1,354 |
| -------------A--- | 70,946 ± 1,326 | 23,662 ± 529 | 10,237 ± 22 |
| --------------A-- | 2,389 ± 473 | 21,401 ± 432 | 2,424 ± 126 |
| ---------------A- | 1,859 ± 110 | 32,035 ± 257 | 36,930 ± 623 |
| ----------------A | 1,569 ± 32 | 31,506 ± 351 | 34,389 ± 457 |
| Medium alone | 1,763 ± 132 | 999 ± 57 | 715 ± 53 |

FIG. 2

T CELL RECEPTOR Vβ-Dβ-Jβ SEQUENCE AND METHODS FOR ITS DETECTION

This is a continuation-in-part of application Ser. No. 09/507,819, filed Feb. 22, 2000, now U.S. Pat. No. 6,303, 314, which claims the benefit of U.S. Provisional application Ser. No. 60/121,311, filed Feb. 23, 1999.

The United States government may own rights in the present invention pursuant to grant number NS36140 from the National Institutes of Health.

BACKGROUND THE INVENTION

1. Field of the Invention

The present invention relates generally to the field of treatment of autoimmune disease, such as multiple sclerosis (MS). More particularly, it concerns a T-cell receptor sequence found in some MS patients, and methods for its detection.

2. Description of Related Art

In humans and other mammals, T cell receptors are found on T cells. T cell receptors comprise α and β chains, with β chains comprising the following regions from N-terminus to C-terminus: Vβ-Dβ-Jβ-Cβ. T cell receptors naturally vary in the Vβ-Dβ-Jβ regions.

When an antigen is presented to the T cells by an antigen-presenting cell (APC), a T cell receptor with variable regions (including Vβ-Dβ-Jβ) that so happen to recognize the antigen binds to the antigen on the APC. The T cell bearing the T cell receptor then undergoes activation (clonal expansion).

The pathogenesis of a number of autoimmune diseases is believed to lie in autoimmune T cell responses to antigens presented normally by the organism. An example of such a disease is multiple sclerosis (MS), which is generally held to arise in T cell responses to myelin antigens, in particular myelin basic protein (MBP). MBP-reactive T cells are found to undergo in vivo activation, and occur at a higher precursor frequency in blood and cerebrospinal fluid in patients with MS as opposed to control individuals. These MBP-reactive T cells produce Th1 cytokines, e.g. IL-2, TNF, and γ-interferon. These Th1 cytokines facilitate migration of inflammatory cells into the central nervous system and exacerbate myelin-destructive inflammatory responses in MS.

A number of regulatory mechanisms can be made use of in the treatment of MS. One such is vaccination with one or more of the limited number of T cell membrane-associated peptides with extracellular domains. Vandenbark, U.S. Pat. No. 5,614,192, discloses treatment of autoimmune diseases by the use of immunogenic T cell receptor peptides of 15 to 30 amino acids comprising at least part of the second complementarity determining region (CDR2) of the T cell receptor. A copending U.S. Patent Application by Zhang (60/099,102) discloses treatment of autoimmune diseases by use of immunogenic T cell receptor peptides in combination with immunogenic T cell activation marker peptides.

One area in which vaccination with T cell receptor peptides can be improved is by determining which, if any, common motifs are found in the T cell receptors of a patient with an autoimmune disease such as MS. If such motifs are found, then the patient can be vaccinated with peptides identical to the motifs, in order to facilitate treatment.

Therefore, it is desirable to have the amino acid sequences of common motifs found in the T cell receptors of patients with autoimmune diseases. It is also desirable to be able to readily detect such motifs in a patient sample by a convenient method, such as PCR. In addition, it is desirable to use peptides identical to the detected motifs to treat a patient with the autoimmune disease.

The present invention discloses such a common motif found in the T cell receptors of a subset of Vβ13.1 T cells, the "LGRAGLTY motif", which has the amino acid sequence Lue Gly Arg Ala Gly Leu Thr Tyr (SEQ ID NO: 3), as well as a method for its ready detection by PCR. This motif is found in some T cell receptors of some T cells that recognize amino acids 83–99 of MBP (hereinafter "MBP83–99"). The motif in the context of this subset of Vβ13.1 T cells may hereinafter be referred to as "Vβ13.1-LGRAGLTY." Peptides identical to the motif can be used to vaccinate patients in order to treat or prevent autoimmune diseases with which Vβ13.1-LGRAGLTY is associated. One such autoimmune disease is MS.

SUMMARY OF THE INVENTION

In one embodiment, the present invention is directed to an oligonucleotide from about 15 to 30 nucleotides in length which comprises at least 10 contiguous nucleotides of SEQ ID NO:1, or a sequence complementary thereto or derived therefrom. Even more preferable is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:, or a sequence complementary thereto. Most preferable is an oligonucleotide, of about 15 to 30 nucleotides in length, which comprises the nucleotide sequence of SEQ ID NO:1, or the sequence complementary thereto.

In a series of further embodiments, the oligonucleotide can be used in amplification or detection of a nucleic acid sequence found in Vβ13.1-LGRAGLTY T cells. In one subseries of such embodiments, the oligonucleotide is used in a primer pair, the primer pair comprising or derived from:

(a) a first primer which is an oligonucleotide is from about 15 to 30 nucleotides in length and comprises at least 10 contiguous nucleotides of SEQ ID NO:1, or a sequence complementary thereto; and (b) a second primer which is an oligonucleotide of about 15 and 30 nucleotides in length that does not comprise the sequence (a), and said second primer sequence can be found in the region from Vβ to Jβ of the Vβ13.1 gene (SEQ ID NO: 2) in T cell receptor T cells, wherein the sequences of (a) and (b) are not found on the same strand of the T cell receptor gene.

Preferably said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto.

In another subseries of such embodiments, the oligonucleotide is used as an oligonucleotide probe, the oligonucleotide probe comprising:

(a) an oligonucleotide from about 15 to 30 nucleotide in length and comprises at least 10 contiguous nucleotides of SEQ ID NO:1, or a sequence complementary thereto; and (b) a labeling moiety.

Preferably, the oligonucleotide, is about 15 to 30 nucleotides in length, and comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto. The labeling moiety is preferably selected from $^{32}$P or digoxingenin.

In another embodiment, the present invention is directed to a method of detecting MBP83–99 Vβ13.1 T cells expressing a LGRAGLTY motif, comprising:
  (i) obtaining a nucleic acid sample from MBP83–99 Vβ13.1 T cells;
  (ii) contacting the nucleic acid sample with a primer pair selected or derived from:
    (a) a first primer comprising an oligonucleotide of about 15 to 30 nucleotides in length and comprises at least 10 contiguous nucleotides of SEQ ID NO:1, or a sequence complementary thereto or derived therefrom; and
    (b) a second primer comprising and oligonucleotide of about 15 and 30 nucleotides in length that does not comprise the sequence of (a) and is found in the region from Vβ to Jβ of the Vβ13.1 gene in Vβ13.1 T cells (SEQ ID NO:2),
    wherein the sequences of (a) and (b) are not found on the same strand of the Vβ13.1 gene; and,
  (iii) detecting the presence of the nucleic acid encoding the LGRAGLTY motif.

Preferably the first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO: 1, or a sequence complementary thereto. Most preferable is an oligonucleotide, of about 15 to 30 nucleotides in length, which comprises the nucleotide sequence of SEQ ID NO:1, or the sequence complementary thereto.

Another embodiment of the present invention is directed to peptides, of from 8 to approximately 45 amino acid residues in length, comprising the LGRAGLTY motif (i.e. comprising the sequence of SEQ ID NO: 3). In various aspects of this embodiment, of the invention, the peptide comprises 8, 9, 10, 11, 12, 13, 14, 15, 16, 17, 18, 19, 20, 21, 22, 23, 24, 25, 26, 27, 28, 29, 30, 31 or 32 contiguous amino acids of the sequence of SEQ ID NO:32. Preferably the peptide sequence is SEQ ID NO:3 or the sequence is residues 2–21 of SEQ ID NO:32. Most preferably the peptide sequences is residues 2–21 of SEQ ID NO:32.

In yet another embodiment, the present invention is directed to a method of treating an autoimmune disease, comprising:
  (a) obtaining MBP83–99 Vβ13.1 T cells from a human;
  (b) detecting the presence of a nucleic acid encoding the LGRAGLTY motif by the method described above; and, if the nucleic acid is detected,
  (c) administering one or more peptides of from 8 to approximately 45 amino acid residues in length, each comprising the LGRAGLTY motif, to the human. In various aspects of this embodiment, of the invention, the peptides administered to the human each comprise 8, 9, 10, 11, 12, 13, 14, 15, 16, 17, 18, 19, 20, 21, 22, 23, 24, 25, 26, 27, 28, 29, 30, 31 or 32 contiguous amino acids of the sequence of SEQ ID NO:32. Preferably the peptide sequence is SEQ ID NO:3 or the peptide sequence is residues 2–21 of SEQ ID NO:32. Most preferably the peptide sequences is residues 2–21 of SEQ ID NO:32.

In a still further embodiment, the present invention is directed to a method of monitoring an autoimmune disease, comprising:
  (a) obtaining MBP83–99 Vβ13.1 T cells from a human;
  (b) detecting the presence of a nucleic acid encoding the LGRAGLTY motif by the method described above; and, if the nucleic acid is detected,
  (c) quantifying the nucleic acid.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 shows reactivity patterns of two MBP83–99 T cell clones to analog peptides with single alanine substitutions. Two pairs of MBP83–99 T cell clones that exhibited identical Vβ13.1 rearrangements (for MS7-E2.6 and MS27-C3.1) and a similar Vα-Jα junctional sequence (for MS7-E2.6 and MS7-E3.1) were examined for reactivity to a panel of alanine substituted peptides in [$^3$H]-thymidine incorporation assays. A mouse fibroblast cell line expressing DRB1*1501 was used as a source of antigen-presenting cells. The proliferative responses of the clones to each analog peptide were measured after 72 hours and the results are presented as CPM incorporated. The shaded boxes represent >50% decrease in the proliferation of the T cell clones in response to analog peptides.

DESCRIPTION OF ILLUSTRATIVE EMBODIMENTS

Figure 1:
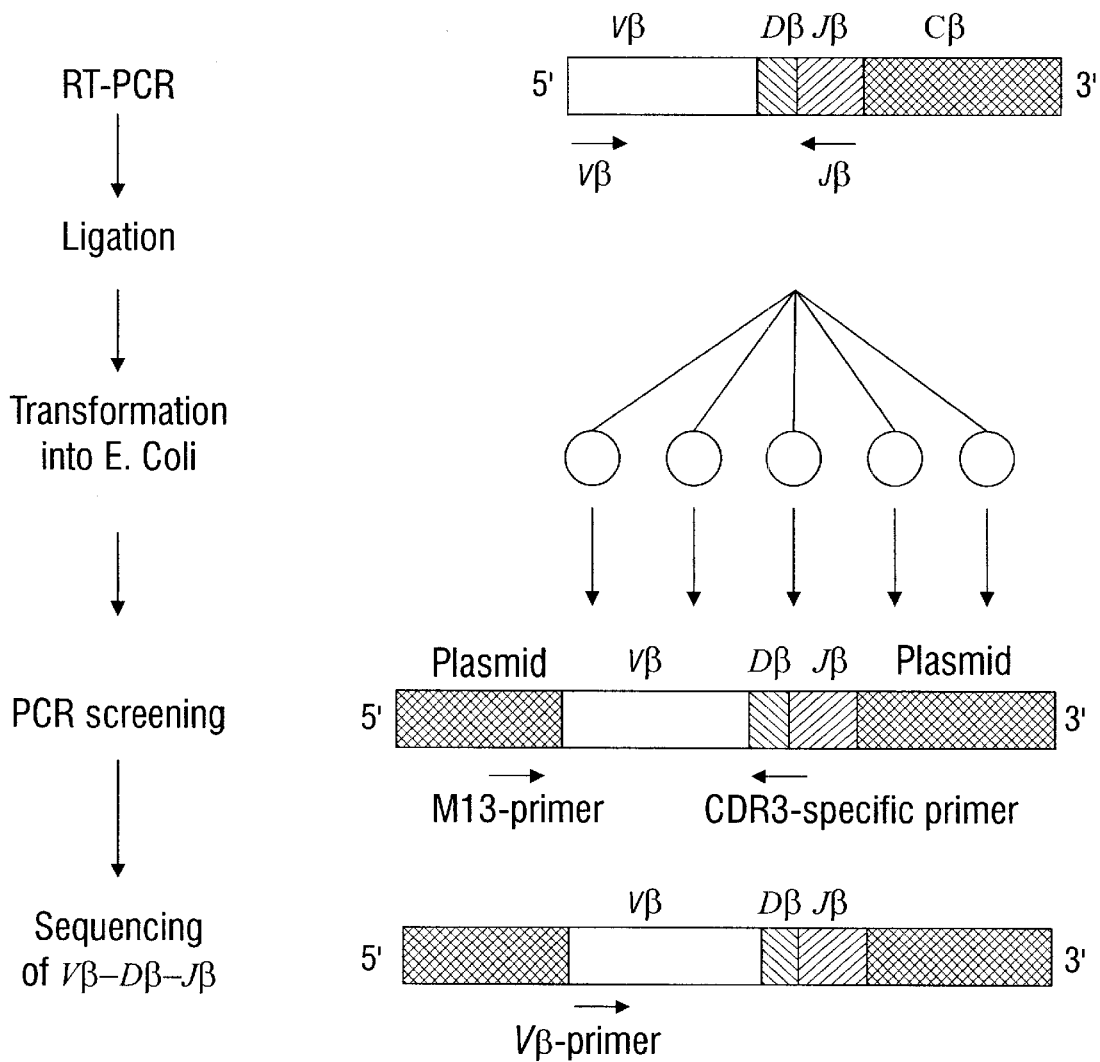
FIG. 1 shows the experimental procedure for cloning and sequencing of PBMC-derived PCR products. cDNA derived from PBMC specimens were amplified by the 5'Vβ13.1 primer and the 3'Jβ primer from four PBMC specimens positive for the expression of the LGRAGLTY motif were ligated into the TA cloning vector pCR2.1 and transformed into E. coli. Plasmid DNA was screened by PCR with a M13 primer and the LGRAGLTY-specific primer. The positive plasmids that showed visible amplification by PCR were sequenced for VβDβJβ sequences with a Vβ13.1 primer.
Figure 3:
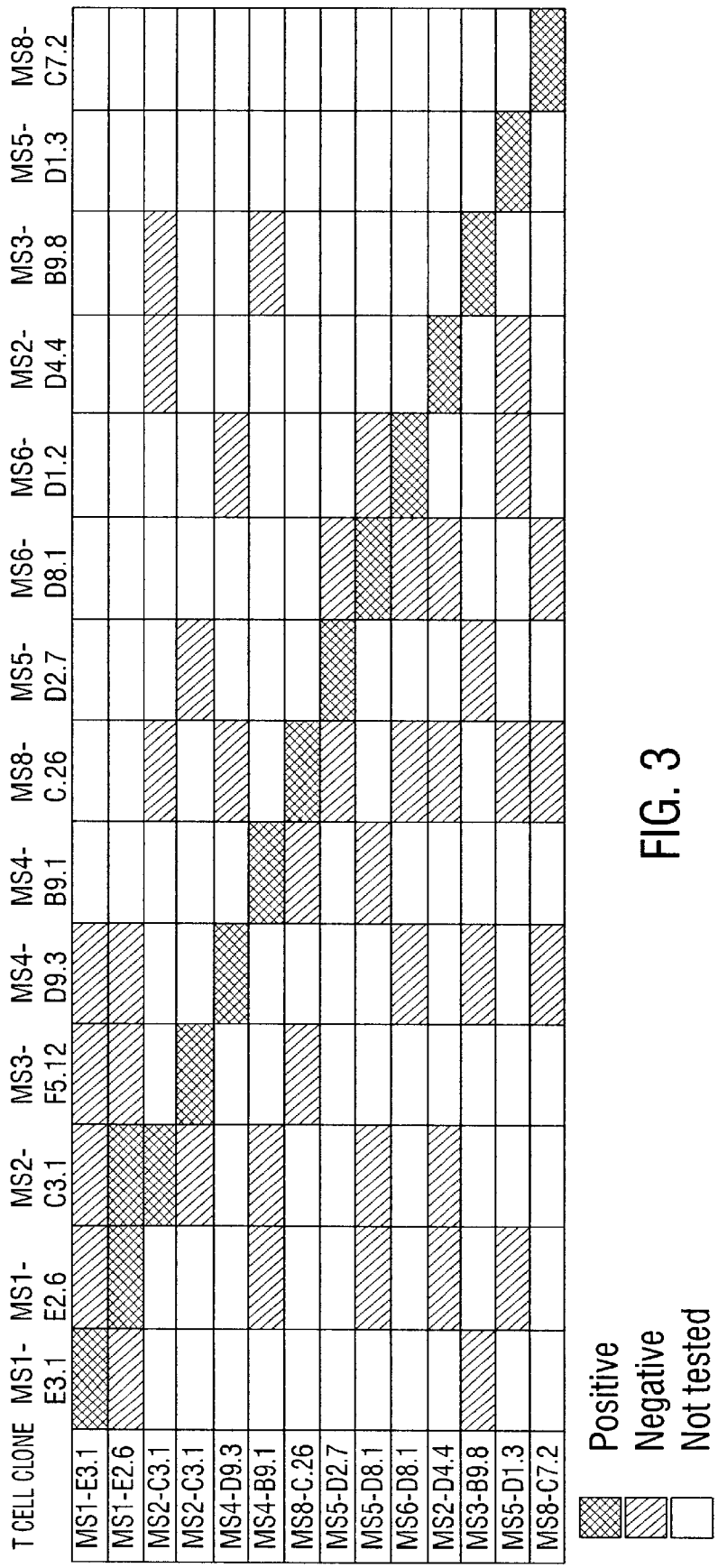
FIG. 3 shows cross-examination of the specificity of CDR3 oligonucleotides with original and unrelated T cell clones. A set of oligonucleotides specific for TCR VDJ region of were examined for their specificity in detecting known target DNA sequences present in original MBP83–99 T cell clones as well as in unrelated MBP83–99 T cell clones derived from the same and different individuals. PCR reactions using CDR3-specific oligonucleotides as the forward primers and a 3'-Cβ primer as the reverse primer performed. Solid boxes represent positive detection of DNA sequences present in original T cell clones or T cell clone(s) sharing the same CDR3 sequences. All primers were also examined for their binding to DNA products of randomly selected T cell clones that had unrelated CDR3 sequences (shaded boxes).
Figure 4:
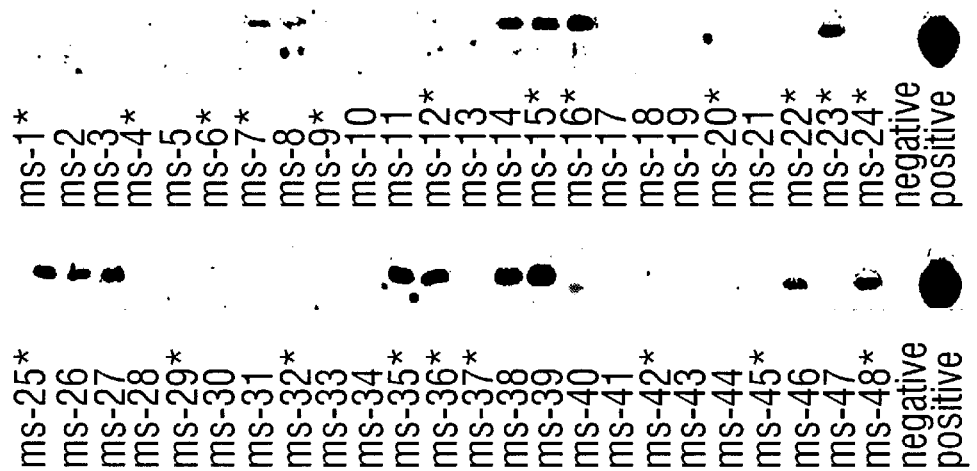
FIG. 4 shows detection of target DNA sequence complementary to motif Vβ13.1-LGRAGLTY in randomly selected PBMC specimens derived from patients with MS. cDNA prepared from PBMC specimens from randomly selected MS patients (n=48) were first amplified in RT-PCR using a 5'-Vβ13.1 specific primer and a 3'-Cβ primer. The amplified PCR products were then hybridized subsequently with a digoxigenin-labeled oligonucleotide probe specific for the LGRAGLTY motif. The original MBP83–99 clone (MS7-E2.6) and an unrelated T cell clone (MS32-B9.8) were used as positive and negative controls, respectively. MS-7 and MS-27 were the original PBMC specimens from which clone MS7-E2.6 (MS-7 in Table 1) and clone MS27-C3.1 (MS-27 in Table 1) were derived. Asterisks indicate positive expression of DRB1*1501.
Figure 5:
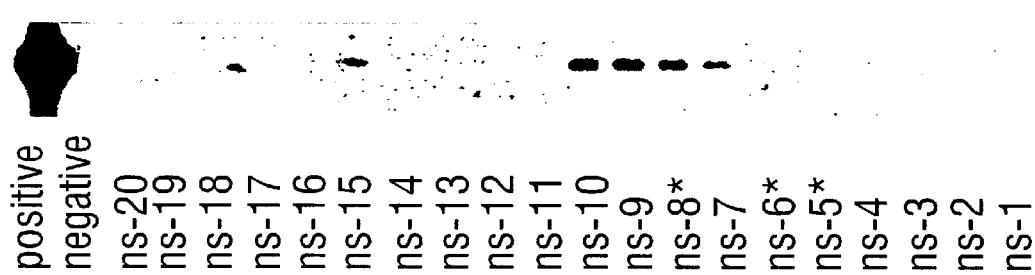
FIG. 5 shows detection of the Vβ13.1-LGRAGLTY motif in randomly selected PBMC specimens derived from normal subjects. PBMC specimens obtained from 20 normal subjects (NS) were analyzed under the same condition as described in the FIG. 4 legend. The original clone (MS7-E2.6) and an unrelated T cell clone (MS32-B9.8) were used as positive and negative controls, respectively. Asterisks indicate positive expression of DRB1*1501.
Figure 6:
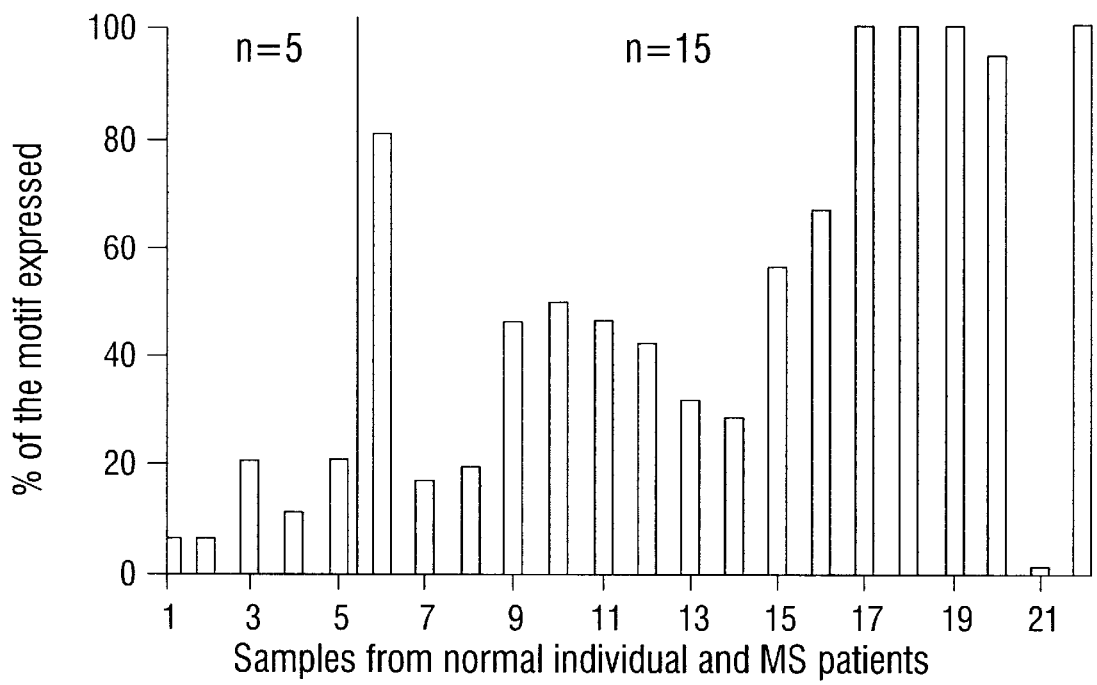
FIG. 6 shows semi-quantitative comparason of the expression of the LGRAGLTY motif in PBMC specimens derived from MS patients and normal subjects. The expression of motif Vβ13.1-LGRAGLTY was analyzed by semi-quantitative PCR relative to the Cβ expression in each cDNA derived from PBMC of MS and normal individuals. The relative expression level was calculated as (expression of the LGRAGLTY motif/Expression of Cβ)×100%.
Figure 7:
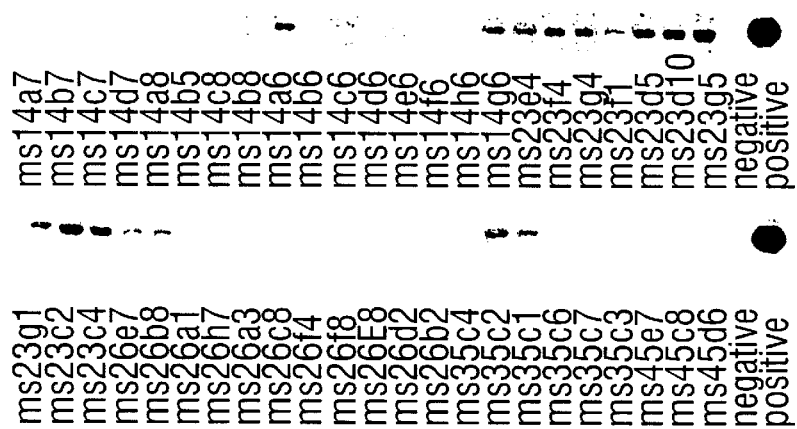
FIG. 7 shows detection of the Vβ13.1-LGRAGLTY motif in short-term MBP83–99 T cell lines derived from patients with MS. A panel of independent short-term MBP83–99 T cell lines were generated from five patients with MS using a synthetic 83–99 peptide of MBP. All these T cell lines were confirmed for their specific reactivity to MBP83–99 peptide (CPM in response to MBP83–99/control CPM>5). cDNA products were amplified using a 5'-Vβ13.1 specific primer and a 3'-Cβ primer in PCR. The amplified PCR products were hybridized subsequently with a digoxigenin-labeled oligonucleotide probe corresponding to the Vβ13.1-LGRAGLTY motif in a Southern blot analysis. cDNA products derived from the original MBP83–99 clone (MS7-E2.6) and a unrelated T cell clone (MS32-B9.8) were used as positive and negative controls, respectively.

To aid in understanding the invention, several terms are defined below.

"PCR" means the polymerase chain reaction, for example, as generally described in U.S. Pat. No. 4,683,202 (issued Jul. 28, 1987 to Mullins), which is incorporated herein by reference. PCR is an amplification technique wherein selected oligonucleotides, or primers, are hybridized to nucleic acid templates in the presence of a polymerization again (such as polymerase) and four nucleotide triphosphates, and extension products are formed from the primers. These products are then denatured and used as templates in a cycling reaction that amplifies the number and amount of existing nucleic acids to facilitate their subsequent detection. A variety of PCR techniques are available and may be used with the methods according to the invention.

"Primer" means an oligonucleotide, whether natural or synthetic, capable of acting as a point of initiation of DNA synthesis complementary to a specific DNA sequence on a template molecule.

"Derived from," in the context of the term "primer(s) or probe(s) derived from," means that the primer or probe is not limited to the nucleotide sequence(s) listed, but also includes variations in the listed nucleotide sequence(s) including nucleotide additions, deletions, or substitutions to the extent that the variations to the listed sequence(s) retain the ability to act as a primer in the detection of T cell receptor DNA encoding the Vβ13.1-LGRAGLTY sequence, i.e. Lue Gly Arg Ala Gly Leu Thr Tyr (SEQ ID NO: 3).

"Immunogenic," when used to describe a peptide, means the peptide is able to induce an immune response, either T cell mediated, antibody, or both. "Antigenic" means the peptide can be recognized in a free form by antibodies and in the context of MHC molecules in the case of antigen-specific T cells.

"Immune-related disease" means a disease in which the immune system is involved in the pathogenesis of the disease. A subset of immune-related diseases are autoimmune diseases. Autoimmune diseases contemplated by the present invention include, but are not limited to, rheumatoid arthritis, myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis, and certain types of diabetes. In view of the present disclosure, one skilled in the art can readily perceive other autoimmune diseases treatable by the compositions and methods of the present invention. "T cell mediated disease" means a disease brought about in an organism as a result of T cells recognizing peptides normally found in the organism.

"Treatment" or "treating," when referring to protection of an animal from a disease, means preventing, suppressing, or repressing the disease. Preventing the disease involves administering a composition of the present invention to an animal prior to induction of the disease. Suppressing the disease involves administering a composition of the present invention to an animal after induction of the disease but before its clinical appearance. Repressing the disease involves administering a composition of the present invention to an animal after clinical appearance of the disease. It will be appreciated that in human medicine it cannot always be known when in the course of disease induction a composition of the present invention will be administered.

In one aspect, the present invention is directed to a primer pair comprising the sequence of or derived from:

(a) a first primer which is an oligonucleotide of about 15 to 30 nucleotides in length, comprising at least 10 contiguous nucleotides of SEQ ID NO: 1, or the nucleic acid sequence complementary thereto; and (b) a second primer which is an oligonucleotide of about 15 and 30 nucleotides in length that does not comprise a sequence of (a) and is found in the region from Vβ to Jβ of the T cell receptor gene in Vβ13.1 T cells, wherein the sequences of(a) and (b) are not found on the same strand of the T cell receptor gene.

Preferably, said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:, or a sequence complementary thereto. Most preferable is an oligonucleotide, of about 15 to 30 nucleotides in length, which comprises the nucleotide sequence of SEQ ID NO:1, or the sequence complementary thereto.

The primers according to the invention are designed to amplify a fragment of a gene encoding T cell receptor of human Vβ13.1 T cells, the fragment comprising an amino acid motif Lue Gly Arg Ala Gly Leu Thr Tyr (SEQ ID NO: 3). The gene from Vβ13.1 T cells encoding the T cell receptor comprising the LGRAGLTY motif has been submitted to GenBank, accession number AF117132. The sequence of the gene from Vβ13.1 T cells encoding the T cell receptor comprising the LGRAGLTY motif is given herein as SEQ ID NO: 2. In the method according to the invention, a fragment of about 400 bp of the T cell receptor gene from Vβ13.1 T cells is amplified using two primers, wherein the first primer is in the CDR3 region, and the second primer is in the Cβ region. The Vβ-Dβ-Jβ region of the T cell receptor gene will be between the CDR3 and Cβ regions, inclusive. In a preferred embodiment, the primers are the primer pair described above.

Primers according to the invention also include oligonucleotides that are derived from the primers (a)–(b). A sequence is derived from a primer (a) or (b) if it has or contains substantially the same sequence as one of the primers and retains the ability to selectively anneal to approximately the same CDR3 or Cβ region of the Vβ-Dβ-Jβ region of the T cell receptor gene from Vβ13.1 T cells as described above. More particularly, the primer may differ from a primer (a) or (b) in length or by the kind of nucleic acid in one or more positions along the sequence, as long as it retains selectivity for the identified regions of the Vβ-Dβ-Jβ region of the T cell receptor gene from Vβ13.1 T cells. For example, the primer may be an oligonucleotide having at least 15 nucleotides, wherein the 15 nucleotides are identical with a series of 15 contiguous nucleic acids selected or derived from a sequence of the primers (a)–(b). The primer may also be any oligonucleotide of about 30 nucleotides or less comprising a segment having the sequence selected or derived from any of primers (a)–(b). The number of nucleotides in the primer should be high enough to retain selectivity, yet low enough to retain efficiency and operability in primer synthesis and the PCR procedure. The primer may have variations including nucleotide deletions, additions, or substitutions to the extent that the variations to the sequence of primers (a)–(b) retain the ability to act as a primer in the detection of Vβ13.1-LGRAGLTY.

The Vβ13.1-LGRAGLTY detection method according to the invention uses a pair of the above primers in a procedure that detects the presence of any Vβ13.1-LGRAGLTY in a sample. The sample to be tested for the presence of Vβ13.1-LGRAGLTY is a nucleic acid, preferably DNA. The DNA can be genomic DNA, cDNA, DNA previously amplified by PCR, or any other form of DNA. The sample can be isolated, directly or indirectly, from any animal or human bodily tissue that expresses T cell receptor β chain genes. A preferred bodily tissue is peripheral blood mononuclear cells (PBMC). If the sample is genomic DNA, it can be isolated directly from the bodily tissue. If the sample is cDNA, it is isolated indirectly by reverse transcription of mRNA directly isolated from the bodily tissue. If the sample is DNA previously amplified by PCR, it is isolated indirectly by amplification of genomic DNA, cDNA, or any other form of DNA.

In a preferred embodiment, a portion of the T cell receptor gene from Vβ13.1 T cells, the portion comprising a sequence encoding the LGRAGLTY motif, is amplified to enhance the ability to detect the presence of Vβ13.1-LGRAGLTY (5'-CTAGGGCGGGCGGGACTCACCTAC-3' (SEQ ID NO: 1)). The amplification can take place via a PCR reaction, using any particular PCR technique or equipment that provides sensitive, selective and rapid amplification of the portion in the sample.

For example, the PCR amplification can follow a procedure wherein a reaction mixture is prepared that contains the following ingredients: 5 μL 10×PCR buffer II (100 mM Tris-HCl, pH 8.3, 500 mM KCl), 3 μL 25 mM MgCl$_2$, 1 μL 10 mM dNTP mix, 0.3 μL Taq polymerase (5 U/μL) (AmpliTaq Gold, Perkin Elmer, Norwalk, Conn.), 30 pmol of primer A, and 30 pmol of primer B. In light of the present disclosure, the skilled artisan will be able to select appropriate primers A and B for the purpose of PCR amplification of the portion of the T cell receptor gene from Vβ13.1 T cells. The above mixture is appropriate for amplifying 1 μL of sample DNA. Hereinafter, the DNA to be amplified may be referred to as the "template."

Once sample DNA is added to the above reaction mixture, the PCR reaction can be performed with an amplification profile of 1 min at 95° C. (denaturation); 20 sec at 56° C. (annealing), and 40 sec at 72° C. (extension) for a total of 35 cycles.

In the PCR reaction, the template can be heat denatured and annealed to two oligonucleotide primers. The oligonucleotides bracket an area of the nucleic acid sequence that is to be amplified. A heat stable DNA polymerase is included in the reaction mixture. The polymerase elongates the primers annealed to complementary DNA by adding the appropriate complementary nucleotides. Preferred polymerases have the characteristics of being stable at temperatures of at least 95° C., have a processivity of 50–60 and have an extension rate of greater than 50 nucleotides per minute.

Approximately 40 PCR cycles are used in a typical PCR amplification reaction. However, certain PCR reactions may work with as few as 15 to 20 cycles or as many as 50 cycles. Each cycle consists of a melting step in which the template is heated to a temperature above about 95° C.

The temperature of the PCR reaction is then cooled to allow annealing of the primers to the template. In this annealing step, the reaction temperature is adjusted to between about 55° C. to 72° C. for approximately 20 seconds. Longer or shorter times may work depending upon the specific reaction.

The temperature of the PCR reaction is then heated to allow maximal elongation of the primers to be effected by the polymerase. In this extension step, the reaction temperature is adjusted to between about 70° C. and 75° C. for approximately 40 seconds. Higher or lower temperatures and/or longer or shorter times may work depending upon the specific reaction.

In addition, before the first cycle is begun, the reaction mixture can undergo an initial denaturation for a period of about 5 min to 15 min. Similarly, after the final cycle is ended, the reaction mixture can undergo a final extension for a period of about 5 min to 10 min.

Amplification can be performed using a two-step PCR. In this technique, a first PCR amplification reaction is performed to amplify a first region that is larger than, and comprises, a region of interest. A second PCR amplification reaction is then performed, using the first region as a template, to amplify the region of interest. If either primer from the first PCR reaction can be used in the second PCR reaction, the second PCR reaction is "semi-nested." If neither primer from the first PCR reaction can be used in the second PCR reaction, the second PCR reaction is "nested."

In a preferred way of performing the method of the present invention, the Vβ13.1-LGRAGLTY motif is amplified by two-step PCR. In the first PCR reaction, the sample is amplified using a first primer that anneals to the Vβ region of the T cell receptor gene and a second primer that anneals to the Cβ region of the T cell receptor gene, using the reaction mixture and profile disclosed above. The first PCR reaction amplifies a first region that is about 600 bp and extends from Vβ through the Vβ-Dβ-Jβ junction to Cβ. The second PCR reaction is nested or semi-nested; a portion of the first region is partially amplified using primer pair (a)–(b). The second PCR reaction amplifies the region of interest.

After amplification of any DNA encoding Vβ13.1-LGRAGLTY in the sample, the amplification product is detected. This detection may be done by a number of procedures. For example, an aliquot of amplification product can be loaded onto an electrophoresis gel, to which an electric field is applied to separate DNA molecules by size. In another method, an aliquot of amplification product is loaded onto a gel stained with SYBR green, ethidium bromide, or another molecule that will bind to DNA and emit a detectable signal. For example, ethidium bromide binds to DNA and emits visible light when illuminated by ultraviolet light. A dried gel could alternatively contain a radio- or chemically-labeled oligonucleotide (which may hereinafter be termed an "oligonucleotide probe") complementary to a portion of the sequence of the amplified template, from which an autoradiograph is taken by exposing the gel to film.

In another embodiment, the present invention relates to an oligonucleotide probe, comprising
(a) a oligonucleotide of about 15 to 30 nucleotides in length, comprising at least 10 contiguous nucleotides of SEQ ID NO:1, or the nucleic acid sequence complementary thereto; and
(b) a labeling moiety.

Preferably "(a)" is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto. Preferably, the labeling moiety is selected from $^{32}$P or digoxingenin.

A typical radiolabeled oligonucleotide useful for detection of amplification products produced using primers of the present invention is taken from the Vβ-Dβ-Jβ region. If the Vβ13.1-LGRAGLTY region is amplified by the two-step semi-nested PCR disclosed above, wherein a primer corresponding to the sequence encoding the LGRAGLTY motif is used, any oligonucleotide of about 10 or more nucleotides, and preferably about 18 or more nucleotides, that is complementary to a portion of either strand of the amplified Vβ13.1-LGRAGLTY region can be used. More preferably, the oligonucleotide 5'-CTAGGGCGGGCGGGACTCACCTAC-3' (SEQ ID NO: 1) or the nucleic acid sequence complementary thereto is used as a probe.

The present invention also comprises a test kit, comprising at a first primer (a) of about 15 to 30 nucleotides in length comprising at least 10 contiguous nucleotides of SEQ ID NO: 1, or an the nucleic acid sequence complementary thereto.

In one preferred embodiment, the test kit further comprises a second primer (b), wherein the second primer is a nucleic acid sequence of about 15 and 30 nucleotides in length that does not comprise the sequence of (a) and is found in the region from Vβ to Jβ of the Vβ 13.1 T cell receptor gene in T cells,
  wherein the sequences of (a) and (b) are not found on the same strand of the T cell receptor gene.

More preferably said first primer is an oligonucleotide, of about 15 to 30 nucleotides in length, which comprises 11, 12, 13, 14, 15, 16, 17, 18, 19, 20, 21, 22, or 23 contiguous nucleotides of SEQ ID NO:1, or a sequence complementary thereto. Most preferable is an oligonucleotide, of about 15 to 30 nucleotides in length, which comprises the nucleotide sequence of SEQ ID NO:1, or the sequence complementary thereto In this embodiment, the test kit further comprises at least one reagent useful in the amplification of Vβ13.1-LGRAGLTY DNA by PCR techniques as described above. Exemplary reagents that can be included in the kit include, but are not limited to, buffers, deoxynucleoside triphosphates, heat-stable DNA polymerase such as Taq polymerase, Vβ13.1-LGPAGLTY DNA for positive control, and non-Vβ13.1-LGRAGLTY DNA for negative control. Other reagents that can be included in the test kit are known to one skilled in the art.

In another preferred embodiment, the test kit further comprises a labeling moiety. Preferably the labeling moiety is $^{32}$P or digoxingenin.

Another embodiment of the present invention is directed to peptides, of from 8 to approximately 45 amino acid residues in length, comprising the LGRAGLTY motif (i.e. comprising the sequence of SEQ ID NO: 3). In various aspects of this embodiment, of the invention, the peptide comprises 8, 9, 10, 11, 12, 13, 14, 15, 16, 17, 18, 19, 20, 21, 22, 23, 24, 25, 26, 27, 28, 29, 30, 31 or 32 contiguous amino acids of the sequence of SEQ ID NO:32. Preferably the peptide sequence is SEQ ID NO:3 or the sequence is residues 2–21 of SEQ ID NO:32. Most preferably the peptide sequences is residues 2–21 of SEQ ID NO:32. In a preferred aspect of this embodiment of the invention the peptides are present as purified peptides. By "purified peptides" it is meant that the majority (greater than 50%) of the polypeptides in the sample are the desired peptide. Preferably, the desired peptides constitute greater than 70% of the peptides in the purified peptide sample. More preferably the peptide constitutes greater than 90% of the peptides in the sample. Even more preferably the peptide constitutes greater than 95% of the polypeptide in the sample. Additionally, the term "purified peptide" indicates that the sample does not contain substances which interfere with the operation of the instant invention.

Peptides according to this aspect of the invention may be from any source compatible with the present invention either natural or synthetic (which may be obtained from commercial sources known to skilled artisans).

Other embodiments of the current invention provide for pharmaceutical compositions comprising the peptides described above. Methods of producing pharmaceutical peptide compositions are known in the art, see for example, U.S. Pat. No. 6,066,619 and 6,068,850 which are herein incorporated by reference. Various aspects of this embodiment of the instant invention may comprise a pharmaceutically acceptable excipient, carrier, or diluent and do not contain any biologically harmful substances. The pharmaceutical compositions of the present invention may be formulated by one having ordinary skill in the art. Exemplary pharmaceutical formulations are also described in *Remington's Pharmaceutical Sciences* (Alfonso R. Gennaro Ed., 16$^{th}$ Edition, 1980), which is a standard reference text in the pharmaceutical field, is herein incorporated by reference.

The pharmaceutical compositions may further comprise coloring or stabilizing agents, osmotic agents, antibacterial agents, or any other substances which do not interfere with the function of the composition. The pharmaceutical compositions of the invention, can, for example, be formulated as a solution, suspension, or emulsion in association with a pharmaceutically acceptable parenteral vehicle. The vehicle may contain additives that maintain isotonicity (e.g., sodium chloride or mannitol) and chemical stability (e.g., buffers and preservatives). It should be appreciated that endotoxin contamination should be kept at a safe level, for example, less than 0.5 ng/mg protein. Moreover, for human administration, preparations should meet sterility, pyrogenicity, general safety, and purity standards as required by the United States Food and Drug Administration Office of Biological Standards. The formulations may be sterilized by commonly used techniques such as filtration.

The phrase "pharmaceutically acceptable" refers to substances and compositions which do not produce an adverse, allergic, or otherwise untoward reaction when administered to an animal, or a human, as appropriate. A substance which caused any of these adverse effects would be classified as "biologically harmful" within the scope of the present invention. Pharmaceutically acceptable substances and compositions may include, but are not limited to solvents, dispersion media, coatings, antibacterial and antifungal agents, isotonic and absorption delaying agents. Except where incompatible with the invention the use of any conventional ingredient is contemplated. Furthermore, supplementary active ingredients which serve some other pharmacologically expedient purpose can also be incorporated into the instant compositions.

The present invention also comprises a method of treating an autoimmune disease. The disease is one in which, for at least some patients, T cell receptors comprising LGRAGLTY are found on Vβ13.1 T cells. Other types of T cells, and/or Vβ13.1 T cells which lack T cell receptors comprising the LGRAGLTY motif, may be presented by the patient. The method comprises:

(a) obtaining MBP83–99 Vβ13.1 T cells from a human;
 (b) detecting the presence of a nucleic acid encoding the LGRAGLTY motif by the method described above; and, if the nucleic acid is detected,
 (c) administering a pharmaceutical composition comprising one or more peptides of from 8 to approximately 45 amino acid residues in length, to the human; wherein each peptide is comprised of the LGRAGLTY motif.

In various aspects of this method the pharmaceutical composition administered to the human comprises one or more peptides having 8, 9, 10, 11, 12, 13, 14, 15, 16, 17, 18, 19, 20, 21, 22, 23, 24, 25, 26, 27, 28, 29, 30, 31 or 32 contiguous amino acids of the sequence of SEQ ID NO:32. Preferably the peptide sequence is SEQ ID NO:3 or the peptide sequence is residues 2–21 of SEQ ID NO:32. Most preferably the peptide sequences is residues 2–21 of SEQ ID NO:32.

The autoimmune disease can be any autoimmune disease in which T cell receptors comprising the LGRAGLTY motif are found on Vβ13.1 T cells. Autoimmune diseases contemplated by the present invention include, but are not limited to, rheumatoid arthritis, myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis, and certain types of diabetes. A preferred autoimmune disease is multiple sclerosis (MS).

If nucleic acid encoding an LGRAGLTY motif is detected by the methods disclosed above, the autoimmune disease can be treated by administering pharmaceutical compositions comprising one or more peptides as described above The pharmaceutical compositions of the present invention can be administered alone, or in combination with a T-cell activation marker peptide. Preferably the pharmaceutical composition is administered in combination with a T-cell activation marker peptide, according to the disclosure of Zhang, U.S. patent application Ser. No. 60/099,102, incorporated herein by reference. Administration of the peptide can lead to an immunogenic response, wherein the patient will develop antibodies and T-cell receptors that recognize and bind to the LGRAGLTY motif of T cell receptors found on Vβ13.1 T cells.

Because Vβ13.1-LGRAGLTY can be present in both patients suffering from MS and normal individuals who are not suffering from the disease, it is envisioned that pharmaceutical compositions of the instant invention can be administered to both patients with MS and normal individuals.

In an alternative embodiment, if nucleic acid encoding an LGRAGLTY motif is detected by the methods disclosed above, the autoimmune disease can be monitored by quantifying the nucleic acid. The greater the amount of the nucleic acid present in a sample, such as PBMC, the greater the number of Vβ13.1 T cells and the greater the likely severity of symptoms of the autoimmune disease. Also, depending on the time between the presentation of elevated Vβ13.1 T cell levels and the appearance of symptoms, the clinician may receive an opportunity to apply treatments intended to minimize the severity of the symptoms and/or treat the disease before the symptoms appear.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

T Cell Receptor Vβ-Dβ-Jβ DNA Sequence and Sequence Motifs Shared Among MBP83–99 Specific T Cell Clones Derived from Different Patients with MS A panel of 20 CD4+ independent T cell clones was generated from seven patients with MS. All T cell clones recognized the 83–99 peptide of myelin basic protein (MBP83–99) in the context of HLA-DR2 as determined by using mouse fibroblast cells (L cells) transfected with DRB1*1501 as antigen-presenting cells. The T cell clones were characterized for TCR V gene rearrangements in reverse-transcript PCR (RT-PCR) using Vα- and Vβ-specific oligonucleotide primers and subsequently sequenced for the Vα-Jα and Vβ-Dβ-Jβ junctional regions. The sequences of the junctional regions are shown in Tables 1 and 2.

Table 1. summarizes the results of analysis with a panel of 20 independent MBP83–99 specific T cell clones characterized according to their Vα gene usage by reverse-transcript PCR using a panel of oligonucleotide primers specific for Vα gene families (the sequence of the unique primers used are indicated by being underlined in the DNA sequence corresponding to each clone). The amino acid sequences of the "Vα", "n", "Jα", and "Cα" portions of each clone are indicated in Table 1. as follows: the "n" portions are underlined, the "Vα" and "Jα" sequences are shown in bold on their respective sides of the "n" sequence, and the "Cα" sequence is shown in normal font without being underlined. The amplified PCR products were hybridized with digoxingenin-labeled Cα cDNA probes and were analyzed subsequently for DNA sequence.

Table 2. summarizes the results of an analysis of a panel of 20 independent MBP83–99 specific T cell clones. The clones were analyzed for Vβ gene usage by reverse-transcript for using a set of oligonucleotide primer specific for twenty-six Vβ gene families (sequence of the specific primer for each clone is indicated by being underlined in the corresponding DNA sequence). The "Vβ", "D", "Jβ", and "Cβ" portions of each clone are indicated in Table 2. as follows: the "D" portions are underlined, the "Vβ" and "Jβ" sequences are shown in boldface type on their respective sides of the "D" sequence, and the remaining sequence, "Cβ", is in normal font (not underlined or emboldened). The amplified PCR products were hybridized with digoxingenin-labeled Cβ cDNA probes and were analyzed subsequently for DNA sequence.

TABLE 1

TCR Vα gene sequence specific for MBP83-99 peptide

| T CELL CLONE (GenBank Accession #) | Vgene | DNA or Amino Acid Sequence | Vα-n-Jα-Cα |
|---|---|---|---|
| MS7-E3.1 (AF117142) | Vα22 | Amino Acid | YFCAL<u>SRGGSN</u>YKLTFGKGTLLTVNPNIQN (SEQ ID NO: 4) |
| | | DNA | TACTTCTGTGCT<u>CTGAGTAGGGGAGGTAGCAACTATA</u> AACTGACATTTGGAAAAGGAACTCTCTTAACCGTGAA TCCAAATATCCAGAAC (SEQ ID NO: 5) |
| MS7-D2.2 (AF117143) | Vα9 | Amino Acid | YYCAL<u>KRNFGN</u>EKLTFGTGTRLTIIPNIQN (SEQ ID NO: 6) |
| | | DNA | TATTAC<u>TGTGCTCTAAAAAGAAAC</u>TTTGGAAATGAGAAAT TAACCTTTGGGACTGGAACAAGACTCACCATCATACCCAA TATCCAGAAC (SEQ ID NO: 7) |
| MS7-E2.6 (AF117144) | Vα17 | Amino Acid | YFCAA<u>SPGGSN</u>YKLTFGKGTLLTVNPNIQN (SEQ ID NO: 8) |
| | | DNA | TACTTCTGT<u>GCAGCAAGCCCCGGAGG</u>TAGCAACTATAAAC TGACATTTGGAAAAGGAACTCTCTTAACCGTGAATCCAAA TATCCAGAAC (SEQ ID NO: 9) |
| MS7-C3.1 (AF117145) | Vα17 | Amino Acid | YFCAA<u>MGDFGN</u>EKLTFGTGTRLTIIPNIQN (SEQ ID NO: 10) |
| | | DNA | TACTTCTGTGCAGC<u>AATGGGGGACTTT</u>GGAAATGAGAAAT TAACCTTTGGGACTGGAACAAGACTCACCATCATACCCAA TATCCAGAAC (SEQ ID NO: 11) |
| MS27-D7.16 (AF117145) | Vα17 | Amino Acid | YFCAA<u>MGDFGN</u>EKLTFGTGTRLTIIPNIQN (SEQ ID NO: 12) |
| | | DNA | TACTTCTGTGCAGCAATGGGGGACTTTGGAAATGAGAAAT TAACCTTTGGGACTGGAACAAGACTCACCATCATACCCAA TATCCAGAAC (SEQ ID NO: 13) |
| MS27-F3.4 (AF117145) | Vα17 | Amino Acid | YFCAA<u>MGDFGN</u>EKLTFGTGTRLTIIPNIQN (SEQ ID NO: 14) |
| | | DNA | TACTTCTGTGCAGCAATGGGGGACTTTGGAAATGAGAAAT TAACCTTTGGGACTGGAACAAGACTCACCATCATACCCAA TATCCAGAAC (SEQ ID NO: 15) |
| MS27-D4.4 (AF117146) | Vα22 | Amino Acid | YFCAL<u>SVAGGTS</u>YGKLTFGQGTILTVHPNIQN (SEQ ID NO: 16) |
| | | DNA | TACTTCTGTGCTCT<u>GAGCGTTGCTGGTGGTACTAGC</u>TATGG AAAGCTGACATTTGGACAAGGGACCATCTTGACTGTCCAT CCAAATATCCAGAAC (SEQ ID NO: 17) |
| MS32-F5.12 (AF117147) | Vα16 | Amino Acid | YYCLV<u>GDAVRPGG</u>GNKLTFGTGTQLKVELNIQN (SEQ ID NO: 18) |
| | | DNA | TACTACTGCCTCGT<u>GGGTGACGCCGTGAGGCCGG</u>AGGA GGAAACAAACTCACCTTTGGGACAGGCACTCAGCTAAAA GTGGAACTCAATATCCAGAAC (SEQ ID NO: 19) |
| MS32-B9.8 (AF117147) | Vα16 | Amino Acid | YYCLV<u>GDAVRPGG</u>GNKLTFGTGTQLKVELNIQN (SEQ ID NO: 20) |
| | | DNA | TACTACTGCCTCGTGGGTGACGCCGTGAGGCCGGAGGA |

TABLE 1-continued

TCR Vα gene sequence specific for MBP83-99 peptide

| T CELL CLONE (GenBank Accession #) | Vgene | DNA or Amino Acid Sequence | Vα-n-Jα-Cα |
|---|---|---|---|
| MS37-D9.3 (AF117148) | Vα3 | Amino Acid | GGAAACAAACTCACCTTTGGGACAGGCACTCAGCTAAAA GTGGAACTCAATATCCAGAAC (SEQ ID NO: 21)<br>YFCAT<u>DAGGT</u>YKYIFGTGTRLKVLANIQN (SEQ ID NO: 22) |
| | | DNA | TACTTCTGT<u>GCTACGGACGCAGGAGGAACC</u>TACAAATACA TCTTTGGAACAGGCACCAGGCTGAAGGTTTTAGCAAATAT CCAGAAC (SEQ ID NO: 23) |
| MS37-B9.1 (AF117149) | Vα16 | Amino Acid | YYCLV<u>GDI</u>DDMRFGAGTRLTVKPNIQN (SEQ ID NO: 24) |
| | | DNA | TACTACTGC<u>CTCGTGGGTGACATCGAT</u>GACATGCGCTTTG GAGCAGGGACCAGACTGACAGTAAAACCAAATATCCAGA AC (SEQ ID NO: 25) |
| MS9-C.26 (AF117150) | Vα3 | Amino Acid | YFCAT<u>SVNTD</u>KLIFGTGTRLQVFPNIQN (SEQ ID NO: 26) |
| | | DNA | TACTTCTGTGCT<u>ACATCGGTTAACACCGACAAGCTCATCTT</u> TGGGACTGGGACCAGATTACAAGTCTTTCCAAATATCCAG AAC (SEQ ID NO: 27) |

TABLE 2

TCR Vβ gene sequence specific for MPB83-99 peptide

| T CELL CLONE (Genbank Accession #) | Vgene | DNA or Amino Acid Sequence | Vβ-D-Jβ-Cβ |
|---|---|---|---|
| MS7-E3.1 (AF117130) | Vβ9 | Amino Acid | YFCASS<u>QDRFWGG</u>TVN<u></u>TEAFFGQGTRLTVVEDLNK (SEQ ID NO: 28) |
| | | DNA | TATTTCTGTGCCA<u>GCAGCCAAGATCGTTTTTGGGGGGG</u> GACGGTGAACACTGAAGCTTTCTTTGGACAAGGCACC AGACTCACAGTTGTAGAGGACCTGAACAAG (SEQ ID NO: 29) |
| MS7-D2.2 (AF117131) | Vβ1 | Amino Acid | YFCASS<u>AMGETQY</u>FGPGTRLLVLEDLKN (SEQ ID NO: 30) |
| | | DNA | TATTTCTGTGCCAGCAGC<u>GCTATGGGAGAGACC</u>CAGT ACTTCGGGCCAGGCACGCGGCTCCTGGTGCTCGAGGA CCTGAAAAAC (SEQ ID NO: 31) |
| MS7-E2.6 (AF117132) | Vβ13.1 | Amino Acid | YFCASS<u>LGRAGLTY</u>EQYFGPGTRLTVTEDLKN (SEQ ID NO: 32) |
| | | DNA | TACTTCTGTGCCAGCAGC<u>CTAGGGCGGGCGGGACTCA CCTAC</u>GAGCAGTACTTCGGGCCGGGCACCAGGCTCAC GGTCACAGAGGACCTGAAAAAC (SEQ ID NO: 33) |
| MS27-C3.1 (AF117132) | Vβ13.1 | Amino Acid | YFCASS<u>LGRAGLTY</u>EQYFGPGTRLTVTEDLKN (SEQ ID NO: 34) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO: 35) |
| MS27-D7.16 (AF117132) | Vβ13.1Y | Amino Acid | YCASS<u>LGRAGLTY</u>EQYFGPGTRLTVTEDLKN (SEQ ID NO: 36) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO: 37) |
| MS27-F3.4 (AF117132) | Vβ13.1 | Amino Acid | YFCASS<u>LGRAGLTY</u>EQYFGPGTRLTVTEDLKN (SEQ ID NO: 38) |
| | | DNA | TACTTCTGTGCCAGCAGCCTAGGGCGGGCGGGACTCA CCTACGAGCAGTACTTCGGGCCGGGCACCAGGCTCAC GGTCACAGAGGACCTGAAAAAC (SEQ ID NO: 39) |
| MS27-D4.4 (AF117133) | Vβ9 | Amino Acid | YFCASS<u>PTVNY</u>GYTFGSGTRLTVVEDLKN (SEQ ID NO: 40) |
| | | DNA | TATTTCTGTGCCA<u>GCAGCCCGACAGTTAACTATGGCTA</u> CACCTTCGGTTCGGGGACCAGGTTAACCGTTGTAGAG GACCTGAACAAG (SEQ ID NO: 41) |

TABLE 2-continued

TCR Vβ gene sequence specific for MPB83-99 peptide

| T CELL CLONE (Genbank Accession #) | Vgene | DNA or Amino Acid Sequence | Vβ-D-Jβ-Cβ |
|---|---|---|---|
| MS32-F5.12 (AF117134) | Vβ13.1 | Amino Acid | YFCASSYSIRGQGNEQYFGPGTRLTVTEDLKN (SEQ ID NO: 42) |
| | | DNA | TACTTCTGTGCCAGCAGTTACTCGATTAGGGGACAGG GTAACGAGCAGTACTTCGGGCCGGGCACCAGGCTCAC GGTCACAGAGGACCTGAAAAAC (SEQ ID NO: 43) |
| MS32-B9.8 (AF117134) | Vβ13.1 | Amino Acid | YFCASSYSIRGQGNEQYFRPGTRLTVTEDLKN (SEQ ID NO: 44) |
| | | DNA | TACTTCTGTGCCAGCAGTTACTCGATTAGGGGACAGG GTAACGAGCAGTACTTCCGGCCGGGCACCAGGCTCAC GGTCACAGAGGACCTGAAAAAC (SEQ ID NO: 45) |
| MS37-D9.3 (AF119246) | Vβ7 | Amino Acid | YLCASSQDRVAPQYFGPGTRLLVLEDLKN (SEQ ID NO: 46) |
| | | DNA | TATCTCTGTGCCAGCAGCCAAGATCGGGTTGCGCCAC AGTACTTCGGGCCAGGCACGCGGCTCCTGGTGCTCGA GGACCTGAAAAAC (SEQ ID NO: 47) |
| MS37-B9.1 (AF117135) | Vβ17 | Amino Acid | YLCASSTRQGPQETQYFGPGTRLLVLEDLKN (SEQ ID NO: 48) |
| | | DNA | TATCTCTGTGCCAGTAGTACCCGGCAAGGACCTCAAG AGACCCAGTACTTCGGGCCAGGCACGCGGCTCCTGGT GCTCGAGGACCTGAAAAAC (SEQ ID NO: 49) |
| MS8-D2.7 (AF117136) | Vβ8 | Amino Acid | YLCASSLGQGAYEQYFGPGTRLTVTEDLKN (SEQ ID NO: 50) |
| | | DNA | TATCTCTGTGCCAGCAGCTTAGGACAGGGGCTTACG AGCAGTACTTCGGGCCGGGCACCAGGCTCACGGTCAC AGAGGACCTGAAAAAC (SEQ ID NO: 51) |
| MS8-A2.7 (AF117136) | Vβ8 | Amino Acid | YLCASSLGQGAYEQYFGPGTRLTVTEDLKN (SEQ ID NO: 52) |
| | | DNA | TATCTCTGTGCCAGCAGCTTAGGACAGGGGCTTACG AGCAGTACTTCGGGCCGGGCACCAGGCTCACGGTCAC AGAGGACCTGAAAAAC (SEQ ID NO: 53) |
| MS8-A1.15 (AF117136) | Vβ8 | Amino Acid | YLCASSLGQGAYEQYFGPGTRLTVTEDLKN (SEQ ID NO: 54) |
| | | DNA | TATCTCTGTGCCAGCAGCTTAGGACAGGGGCTTACG AGCAGTACTTCGGGCCGGGCACCAGGCTCACGGTCAC AGAGGACCTGAAAAAC (SEQ ID NO: 55) |
| MS8-D1.3 (AF117137) | Vβ8 | Amino Acid | YFCASSLQVYSPLHFGNGTRLTVTEDLNK (SEQ ID NO: 56) |
| | | DNA | TACTTCTGTGCCAGCAGTTTACAAGTGTATTCACCCCT CCACTTTGGGAACGGGACCAGGCTCACTGTGACAGAG GACCTGAACAAG (SEQ ID NO: 57) |
| MS33-D1.2 (AF117138) | Vβ12 | Amino Acid | YFCAISESIGTGTEAFFGQGTRLTVVEDLNK (SEQ ID NO: 58) |
| | | DNA | TACTTCTGTGCCATCAGTGAGTCGATTGGTACGGGAA CTGAAGCTTTCTTTGGACAAGGCACCAGACTCACAGT TGTAGAGGACCTGAACAAG (SEQ ID NO: 59) |
| MS33-D3.3 (AF117138) | Vβ12 | Amino Acid | YFCAISESIGTGTEAFFGQGTRLTVVEDLNK (SEQ ID NO: 60) |
| | | DNA | TACTTTCTGTGCCATCAGTGAGTCGATTGGTACGGGAA CTGAAGCTTTCTTTGGACAAGGCACCAGACTCACAGT TGTAGAGGACCTGAACAAG (SEQ ID NO: 61) |
| MS33-D8.1 (AF117139) | Vβ3 | Amino Acid | YLCASRDRSYEQYFGPGTRLTVTEDLKN (SEQ ID NO: 62) |
| | | DNA | TACCTCTGTGCCAGCCGGGACAGGTCCTACGAGCAGT ACTTCGGGCCGGGCACCAGGCTCACGGTCACAGAGGA CCTGAAAAAC (SEQ ID NO: 63) |
| MS9-C.26 (AF117140) | Vβ12 | Amino Acid | YFCAISEGSSSGNTIYFGEGSWLTVVEDLNK (SEQ ID NO: 64) |
| | | DNA | TACTTCTGTGCCATCAGTGAGGGGTCCAGCTCTGGAA ACACCATATATTTTGGAGAGGGAAGTTGGCTCACTGT TGTAGAGGACCTGAACAAG (SEQ ID NO: 65) |
| MS35-C7.2 (AF117141) | Vβ2 | Amino Acid | FYICSAIDGYTFGSGTRLTVVEDLNK (SEQ ID NO: 66) |
| | | DNA | TTCTACATCTGCAGTGCTATAGACGGCTACACCTTCGG TTCGGGGACCAGGTTAACCGTTGTAGAGGACCTGAAC AAG (SEQ ID NO: 67) |

Although the Vα and Vβ rearrangements varied between individual MBP83–99 T cell clones, many of these independent T cell clones derived from a given individual shared identical Vα and Vβ chains with the same Vα-Jα and Vβ-Dβ-Jβ junctional region sequences. The finding is consistent with in vivo clonal expansion of MBP83–99 specific T cells in given patients with MS as reported previously (Vandevyver 1995, Wucherpfenning 1994).

Interestingly, as indicated in Tables 1 and 2, an independent T cell clone (clone E2.6) derived from one patient (MS-1) shared the same Vβ13.1 and Vα17 with 3 of 4 T cell clones (clones C3.1, D7.16 and F3.4) obtained from another patient (MS-2). Vβ13.1 of these T cell clones shared an identical DNA sequence within the Vβ-Dβ-Jβ junctional region.

Example 2

Vβ-Dβ-Jβ-Specific Oligonucleotide Primers were Highly Specific and Sensitive in Detecting Corresponding DNA Sequences Present in Original MBP83–99 T Cell Clones as well as in PBMC Containing Original MBP83–99 T Cells A set of 14 oligonucleotide primers were synthesized according to DNA sequences within the Vβ-Dβ-Jβ junctional regions of independent MBP83–99 T cell clones and subsequently examined for their specificity in RT-PCR. The DNA sequences of these oligonucleotide primers are shown in Table 3.

TABLE 3

DNA sequences of Vβ-Dβ-Jβ specific oligonucleotide primers

| T cell clone | DNA sequence | SEQ ID NO |
|---|---|---|
| MS1-E3.1 | AGCAGCCAAGATCGTTTTTGG | SEQ ID NO: 68 |
| MS1-E2.6 | CTAGGGCGGGCGGGACTCACCTAC | SEQ ID NO: 69 |
| MS2-C3.1 | CTAGGGCGGGCGGGACTCACCTAC | SEQ ID NO: 70 |
| MS2-D4.4 | | |
| MS3-F5.12 | TACTCGATTAGGGGACAGGGTAAC | SEQ ID NO: 71 |
| MS3-B9.8 | | |
| MS4-D9.3 | CAAGATCGGGTTGCGCCA | SEQ ID NO: 72 |
| MS4-B9.1 | ACCCGGCAAGGACCTCAAGAGACC | SEQ ID NO: 73 |
| MS5-D2.7 | AGCTTAGGACAGGGGGCT | SEQ ID NO: 74 |
| MS5-D1.3 | | |
| MS6-D8.1 | GCCAGCCGGGACAGGTCC | SEQ ID NO: 75 |
| MS6-D1.2 | GAGTAGATTGGTACGGGA | SEQ ID NO: 76 |
| MS7-C.26 | | |
| MS8-C7.2 | TACATCTGAAGTGCTATAGAC | SEQ ID NO: 77 |

These Vβ-Dβ-Jβ-specific primers bound exclusively to DNA sequences present in the original MBP83–99 T cell clones and did not bind to the sequences derived from unrelated MBP83–99 T cell clones (FIG. 2), suggesting their high specificity for the original Vβ-Dβ-Jβ DNA sequences. The only exception was noted for clone MS1-E2.6 and clone MS2-C3.1, in which the same primer bound to a Vβ-Dβ-Jβ junctional DNA sequence shared by both T cell clones.

Given the specificity of the Vβ-Dβ-Jβ oligonucleotide primers and high sensitivity of PCR detection system, we asked whether this two-step PCR detection system using 5' Vβ primers and Vβ-Dβ-Jβ-specific oligonucleotide primers could be used to detect corresponding Vβ-Dβ-Jβ DNA sequences present in peripheral blood mononuclear cells (PBMC) specimens from which the MBP83–99 T cell clones originated. The results of two separate experiments showed positive detection of the Vβ-Dβ-Jβ sequences in original PBMC specimens. Thus, the findings demonstrated that the PCR detection system where Vβ-Dβ-Jβ sequence served as a fingerprint was specific and sensitive in tracing MBP83–99 T cells present in peripheral blood mononuclear cells by probing identical DNA sequences.

Example 3

The Detection of a Common Vβ-Dβ-Jβ DNA Sequence in PBMC Specimens Derived from Different Patients with MS and Healthy Individuals Next, we examined whether DNA sequences corresponding to Vβ-Dβ-Jβ junctional regions of the MBP83–99 T cell clones could be detected in PBMC specimens randomly selected from a group of patients with MS and healthy individuals. The same PCR amplification system using primers specific for corresponding Vβ families (in the first PCR) and primers specific for Vβ-Dβ-Jβ sequences (in the second semi-nested PCR) was employed. It was combined with Southern blot analysis with corresponding Vβ-Dβ-Jβ probes to perform hybridization. Given the specific requirements of the two-step PCR detection system and specificity of the Vβ-Dβ-Jβ primers and probes, the identified DNA sequences would derive from specific TCR Vβ chains and represent either identical or similar to Vβ-Dβ-Jβ sequences of interest.

The results indicated that only one Vβ-Dβ-Jβ oligonucleotide primer (MS1-E2.6, Vβ13.1-LGRAGLTY) detected complementary TCR Vβ13.1 DNA sequence in 15 of 48 (31%) PBMC specimens obtained from different patients with MS. Thus, the finding indicates the presence of MBP83–99 T cells expressing Vβ13.1-LGRAGLTY in these patients with MS. Under similar experimental conditions, the same primer also detected corresponding DNA sequence in 5 of 20 (25%) PBMC specimens derived from healthy individuals. The remaining 13 Vβ-Dβ-Jβ primers failed to identify any sequence signals in the same panel of PBMC specimens. The results were reproducible in three separate experiments. The identified DNA products amplified by the E2.6 primer originated from T cells expressing Vβ13.1 because a Vβ13.1-specific primer was used in the first PCR for amplification.

Furthermore, the identified Vβ13.1-LGRAGLTY sequence was also amplified in 13 of 24 (54%) short-term MBP83–99 T cell lines generated from five patients with MS (MS-35, MS36 and MS39) whose PBMC specimens were shown to contain the Vβ13.1-LGRAGLTY sequence. The results thus confirmed that the Vβ13.1-LGRAGLTY DNA sequence detected in the PBMC specimens originated from T cells recognizing MBP83–99. The finding also suggests that MBP83–99 T cells expressing the Vβ13.1-LGRAGLTY sequence represent all or the majority of MBP83–99 T cell lines found in some patients with MS.

A combined PCR-DNA hybridization detection system where Vβ-Dβ-Jβ sequences were used as a fingerprint provided a powerful tool in tracing antigen-specific T cells by detecting identical Vβ-Dβ-Jβ junctional sequences. The high specificity and sensitivity of the detection system allowed the identification of specific Vβ-Dβ-Jβ sequences in peripheral blood T cells. The present study demonstrated for the first time that a common subset of Vβ13.1 T cells that recognize the immunodominant 83–99 peptide of MBP and uniformly express an identical Vβ-Dβ-Jβ sequence is present in approximately 30% of patients with MS. The conclusion is made based on step-wise experiments described herein. First, the identical DNA sequence (Vβ13.1-LGRAGLTY) was found among independent MBP83–99 T cell clones derived from different patients with MS. Second, the sequence was identified in cDNA products amplified from TCR Vβ13.1 of PBMC specimens obtained from different patients with MS. Third, the DNA sequence was detected in short-term independent MBP83–99 T cell lines generated from PBMC specimens that were shown to contain the Vβ13.1-LGRAGLTY sequence. MBP83–99 T cells expressing the Vβ13.1-LGRAGLTY sequence seem to represent all or the majority of the MBP83–99 T cell lines generated from some patients with MS. Finally, the presence of Vβ13.1-LGRAGLTY sequence in PBMC specimens was confirmed by recombinant DNA cloning and direct DNA sequencing.

Furthermore, it is not surprising that MBP83–99 T cells expressing the common Vβ13.1-LGRAGLTY sequence are also present in some healthy individuals. Studies reported so far indicate that MBP-reactive T cells, including T cells recognizing the immunodominant 83–99 peptide, are also present in some healthy individuals (Zhang 1994, Ota 1990). However, there is a functional difference that these T cells undergo in vivo activation and clonal expansion in patients with MS, as opposed to healthy individuals (Zhang 1994).

These Vβ13.1 MBP83–99 T cells sharing the common Vβ-Dβ-Jβ sequence may represent a significant fraction of MBP83–99 T cells found in some patients with MS. This possibility is supported by the observation that the Vβ13.1-LGRAGLTY sequence was present in 40% of short-term MBP83–99 T cell lines generated from patients with MS after two stimulation cycles.

The identified common Vβ-Dβ-Jβ sequence may be used as a specific marker in a quantitative PCR detection system to detect a common subset of MBP83–99 T cells in the blood and cerebrospinal fluid in a large group of MS patients for the purpose of monitoring in vivo clonal expansion and in vivo activity potentially associated with the disease. This method will be superior to conventional cell culture-based assays because in vitro selection and expansion of MBP-reactive T cells are often hampered by various inhibitory factors inherent in cell culture. This is consistent with a recent study where the frequency of MBP-reactive T cells was found to be surprisingly high in patients with MS when direct ex vivo analysis was employed to quantify MBP-reactive T cells (Hafler as last author JEM 1997).

Furthermore, synthetic peptides corresponding to the TCR have been shown to induce anti-idiotypic T cell responses to MBP-reactive T cells in patients with MS (Chou et al, J.I.). Therefore, a TCR peptide containing a common CDR3 sequence may be of great potential in eliciting anti-idiotypic T cells to suppress a specific subset of MBP-reactive T cells in a group of patients whose MBP83–99 T cells bear the common CDR3 sequence motif. Immunization with such a common CDR3 peptide would be advantageous over CDR2 peptides or individual-dependent CDR3 peptides as a potential treatment procedure in patients with MS (Vandenbark 1996).

Example 4

Induction of Immune Responses to Immunizing MBP-reactive T Cell Clones and a 20-mer TCR Peptide by T Cell Vaccination in Patients with MS and the Generation of B Cell Lines Producing Specific Antibodies to the TCR Peptide Incorporating the Common CDR3 Sequence from Immunized Patients It has been demonstrated that subcutaneous inoculations with irradiated autologous MBP-reactive T cell clones induced substantial anti-idiotypic T cell responses in patients with MS, which correlated with progressive depletion of circulating MBP-reactive T cells used for vaccination (Medaer et al., 1995)

Materials and Methods
Reagents and Peptides

Medium used for cell culture was Aim-V serum-free medium (Life Technologies, Grand Island, N.Y.). The immunodominant peptide (residues 83–99) of MBP and two TCR peptides of 20 amino acids were synthesized by Chiron Mimotope (San Diego, Calif.). The purity of the peptides was greater than 95%.

Estimation of the Precursor Frequency of MBP-reactive T Cells

PBMCs were plated at 200,000 cells/well (for a total of 96 wells) in the presence of MBP (40 μg/mL). Seven days later, all cultures were restimulated with MBP in the presence of irradiated autologous PBMCs. After another week each well was split into four aliquots (approximately $10^4$ cells per aliquot) and cultured in duplicate with $10^5$ irradiated autologous PMBCs in the presence and the absence of MBP. Cultures were kept for three days and pulsed with [$^3$H] thymidine (Nycomed Amersham, Arlington Heights, Ill.) at one μCi per well during the final 16 hours of culture. Cells were then harvested using an automated cell harvester, and [$^3$H]thymidine incorporation was measured.

A well/culture was defined as specific for MBP or the peptides of MBP when the counts per minute (CPM) were greater than 1000 and exceeded the reference CPM (in the absence of MBP) by at least three fold. The precursor frequency of MBP-reactive T cells was then estimated by dividing the number of specific wells by the total number of PBMCs ($19.2 \times 10^6$ cells) seeded in the initial culture.

Myelin-Reactive T Cell Clones

The positively identified T cell lines were cloned using limiting dilution assay in the presence of phytohemaglutinin-protein (PHA-P) at 2 μg/ml. Cultures were fed with fresh media every three to four days. Growth positive wells were tested for specific reactivity to the MBP83–99 peptide in proliferation assays. The resulting MBP83–99 specific T cell clones were further characterized and used for T cell vaccination.

TCR V Gene Analysis and DNA Sequencing

T cell receptor V gene rearrangements of the immunizing MBP-reactive T cell clones were analyzed using reverse-transcribed PCR. TCR α and β chain genes were amplified and directly sequenced as described elsewhere (Vandevyer et al., 1995; Zhang, Y. C. Q. et al. 1998). Briefly, total RNA was extracted from $10^6$ cells of each MBP83–99 reactive T cell clone using RNeasy mini kit (QIAGEN, Santa Clarita, Calif.). First-strand cDNA reverse transcribed from total RNA was subjected to PCR amplification with a set of primers specific for TCR Vα and Vβ gene families whose sequences were published (Vandevyer et al., 1995; Zhang, Y. C. Q. et al. 1998). The amplified PCR products were separated in a 1% agarose gel by electrophoresis and stained with ethidium bromide. The visualized PCR products were cut and purified subsequently using a QIAquick® gel extraction kit (QIAGEN, Santa Clarita, Calif.), before sequence analysis. The purified PCR products were directly sequenced with the T7 sequencing kit (Pharmacia, Uppsala, Sweden). 1.5 μg of template was sequenced with 2 pmol of the corresponding V gene primer using the method of dideoxy chain termination.

Immunization of MS Patients with Irradiated Autologous MBP-reactive T Cell Clones Two patients with clinically definite MS confirmed by magnetic resonance imaging were included in this study.

They were diagnosed as having relapsing-remitting MS for more than two years. The patients had not taken any immunomodulatory drugs at least three months prior to the study. Immunizations with irradiated autologous MBP83–99 reactive T cell clones was performed as previously described (J. Zhang et al. 1992, 1993). Briefly, MBP83–99 reactive T cell clones was activated and expanded in the presence of PHA seven days prior to injection. T cells were then irradiated at 10,000 rads (using a $^{60}$Co source) and thoroughly washed with sterile saline. A total of $4\times10^7$ cells from two autologous T cell clones was resuspended in 2 ml of sterile saline and were injected subcutaneously in the arms. Each patient received a total of four injections at a two-month interval to achieve adequate immune responses as defined by the proliferation of PBMC to the immunizing T cell clones. The protocol was approved by the Institutional Human Subjects Committee at Baylor College of Medicine. Consent forms were obtained from the patients after explaining the experimental procedures. The patients were evaluated for adverse events and disability score (Expanded Disability Scale Score) before and after each immunization. Gadolinium enhanced MRI scans were performed before and at different time points after immunization. The clinical and radiographic evaluation was part of a separate clinical study.

The Generation of Antibody-producing B Cell Lines by EBV Transformation

The method is described elsewhere (J. Zhang, 1989, 1991). Briefly, PBMC were plated out at 20,000 cells/well in microtiter plates (Costar, Cambridge, Mass.) in the presence of cell-free supernatant of B95.8 line producing EBV (ATCC, Bethesda, Md.) and 0.5 µg/ml Cyclosporin A (Sandoz, Basel, Switzerland) to selectively inhibit T cell growth. Cells were cultured for 14 days with changes of medium every 3–4 days. On Day 14, the growth positive wells were visualized and the culture supernatants were harvested for testing. The precursor frequency of B cells producing specific antibodies was estimated by dividing the number of positive wells by the total number of PBMC plated. Positive B cell lines were transferred subsequently to 24-well plates (Costar, Cambridge, Mass.) for expansion. The B cell lines typically produced 2–10 µg/ml of relatively pure antibodies.

Detection of Anti-TCR Antibody by ELISA

Culture supernatants were collected from individual B cell lines and tested for the presence of anti-idiotypic antibodies using ELISA. Briefly, microtiter plates were coated overnight at 4° C. with the motif-positive TCR peptide or the control TCR peptide, respectively, at a concentration of 1 µg/ml. Wells ere then blocked at 37° C. for two hours with PBS containing 2% bovine serum albumin (BSA) (Sigma, St. Louis, Mo.) and washed four times with 0.02% Tween®20 (Sigma, St. Louis, Mo.) in a 0.9% NaCl solution. Each sample and its control were added to the adjacent wells and incubated for 2 hours. Plates were washed four times and incubated for 30 minutes with a goat anti-human IgG/1 gM antibody conjugated with horseradish peroxidase at 1:1500 dilution (Sigma, St. Louis, Mo.). 0.0125% tetramethylbenzidine/0.008% $H_2O_2$ in citrate buffer (pH=5.0) was used as a substrate, and color development was stopped using 2N $H_2SO_4$. Optical densities were measured using an ELISA reader (Biorad, Hercules, Calif.). Wells containing medium alone served as background control.

Immunoblot Analysis

Lysates were prepared from a representative MBP-reactive T cell clone (MS7.E2.6) expressing the common CDR3 sequence using a standard method described elsewhere (Hjelmeland et al., 1984). Briefly, $5\times10^6$ T cells were lysed in 100 µl lysis buffer containing 150 M NaCl, 50 mM Tris (pH7.6), 0.5% Triton X-100, 1 mM PMSF, 10 µg/ml aprotinin, 10 µg/ml leupeptin. Cell debris were spun down at 13,000 g for 20 min at 4 C. The resulting lysates were electrophoresed using 10% SDS-PAGE. After blotting, nitrocellulose membranes were cut into strips and then blocked with 5% low-fat milk power in Tris-buffered saline containing 0.1% Tween®20 (milk-TBST). The strips were then incubated with undiluted supernatants in mini-incubation trays for one hour at room temperature. A goat anti-human IgG and IgM (heavy+light chains) coupled to horseradish peroxidase was used as secondary antibody (100 ng/ml in 2% milk—TBST) and incubated with washed strips for 45 min. followed by enhanced chemiluminescent visualization of the proteins on membrane (Amersham, Piscataway, N.J.). Supernatant obtained from an EBV-transformed B cell line producing non-reactive antibodies was used as a negative control. A rabbit polyclonal anti-human TCR-beta chain antibody (Santa Cruz Biotechnology, Santa Cruz, Calif.) was included as a positive control.

Flow Cytometry

A representative MBP-reactive T cell clone (MS7-E2.6) expressing the common CDR3 sequence was incubated with the anti-idiotypic antibodies derived from individual B cell lines at 4° C. for 30 min. Supernatant obtained from an EBV-transformed B cell line producing non-reactive antibodies was used as a control. After washing with FACS-buffer (PBS containing 5% fetal calf serum and 0.01% sodium azide) by centrifugation at 2300 rpm for 2 minutes at 4° C., cells were resuspended and stained with a goat anti-human IgG/IgM antibody conjugated with fluorescein (FITC). After two washes the cells were resuspended in 300 µl FACS-buffer and analyzed by flow cytometry using a FACScan (Becton Dickinson, San Jose, Calif.). FITC-conjugated anti-IgG$_1$ was used to detect background staining (Becton Dickinson, San Jose, Calif.).

The Inhibition Assay 20,000 cells of the immunizing MBP-reactive T cell clones (motif-positive and motif-negative T cell clones) were cultured in 150 µl with irradiated autologous PBMC (100,000 cells/well) in the presence and absence of the 83–99 peptide of MBP (20 µg/ml). Fifty µl of undiluted supernatants were added into each well. Cell proliferation was measured after 72 hours in [$^3$H]-thymidine incorporation assays. Supernatant obtained from an EBV-transformed B cell line producing non-reactive antibodies was used as a control.

RESULTS

The Functional and Structural Characteristics of the Immunizing MBP-reactive T Cell Clones A panel of four MBP-reactive T cell clones was generated from two patients with relapsing-remitting MS. These T cell clones expressed the CD4 phenotype and recognized the 83–99 immunodominant peptide of MBP in the context of DR4 or DR2 (DRB1*1501) molecules. They were analyzed for TCR V gene rearrangements by RT-PCR using Vα and Vβ specific primers and subsequently sequenced for the Vα-Jα and Vβ-Dβ-Jβ junctional regions. An independent T cell clone (E2.6) derived from patient MS7 shared the same TCR Vα17 and Vβ13.1 genes with another T cell clone (C3.1) obtained from a different patient (MS27). The two T cell clones had an identical sequence, SEQ ID NO: 3 within the Vβ13.1-Dβ-Jβ junctional region while their Vα17 chains had two distinct Vα-Jα junctional region sequences. As noted supra, the identified LueGlyArgAlaGlyLeuThrTyr (SEQ ID NO:3) sequence represented a common CDR3 motif among Vβ13.1 T cells that recognize the 83–99 immunodominant region of MBP in different patients with MS(23).

Figure 8B:
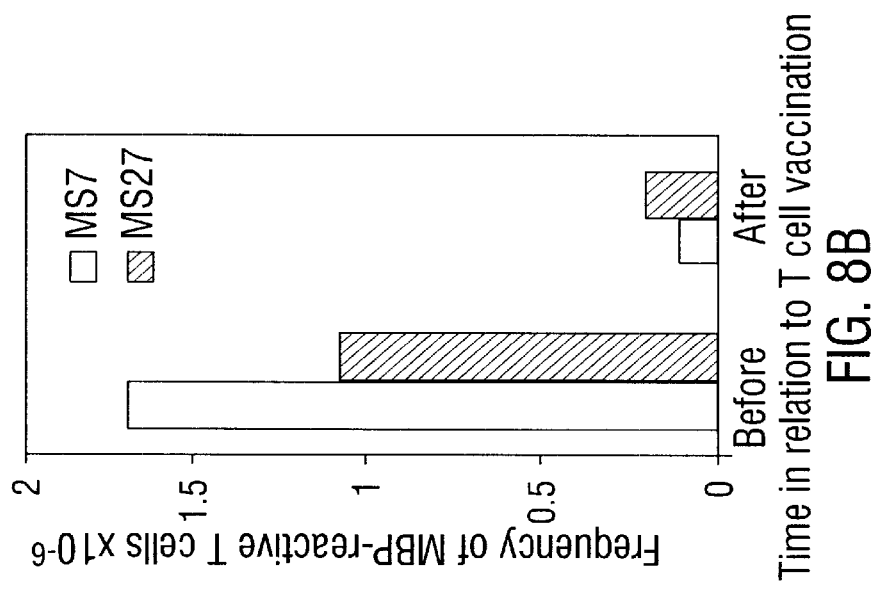
FIG. 8A shows the proliferative responses of PBMCs (peripheral blood mononuclear cells) to the immunizing MBP-reactive T cell clones and the TCR peptides in relationship to the frequency of MBP-reactive T cells in immunized MS patients. 8A: The proliferative responses of PBMCs obtained from two immunized patients are expressed as stimulation indices, which were defined as follows. Counts/minute (CPM) of PBMC cultured with irradiated immunizing MBP-reactive T cell clones expressing the common CDR3 sequence (motif-positive T cell clones, MS7-D2.2 and MS27-D4.4)/the sum of CPM of PBMC cultured alone and CPM of irradiated T cells cultured alone. The proliferative response to the motif-positive peptide (amino acids 2–21 of SEQ ID NO: 32) and a control TCR peptide (amino acids 1–20 of SEQ ID NO: 48) were determined in proliferation assays in which PBMCs were cultured at 100,000 cells/well with the TCR peptides (20 μg/ml), respectively7, for 5 days. All experiments were performed at two time points corresponding to baseline (before) and 2 months after the fourth vaccination (after). 8B: The precursor frequency of T cells specific for MBP was estimated at the same time points. NS=normal subjects.
Figure 8A:
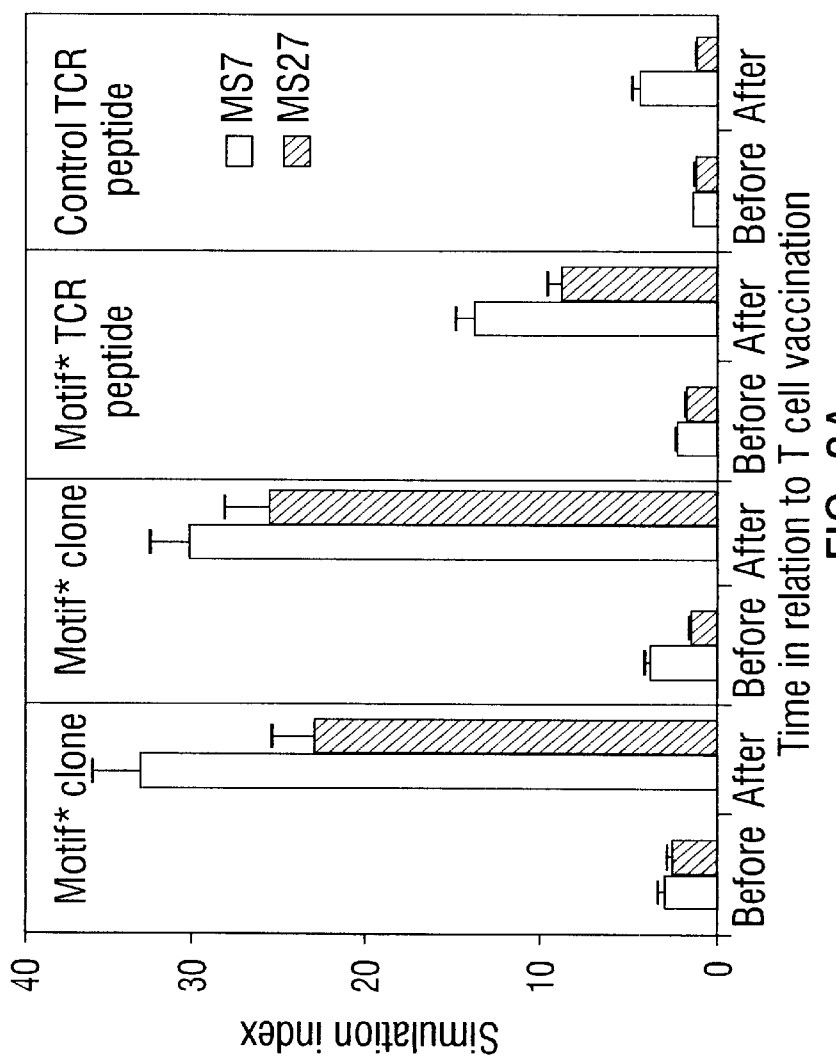

Induction of the Immune Responses to the Immunizing MBP-reactive T Cell Clones and a 20-mer TCR Peptide by T Cell Vaccination in Patients with MS Each patient received a total of four subcutaneous inoculations with two irradiated autologous MBP-reactive T cell clones ($2 \times 10^7$ cells per clone) at a two-month interval. The proliferative responses of PBMC to the autologous immunizing T cell clones were examined at two time points corresponding to baseline and two months after the last immunization. As shown in FIG. 8A, the proliferative responses to both irradiated immunizing T cell clones were increased in the patients after T cell vaccination and exceeded substantially the baseline value. Furthermore, the responses to the TCR peptide incorporating the common CDR3 sequence (motif-positive peptide, consisting of amino acids 2–21 of SEQ ID NO: 32), as opposed to a control CDR3 peptide (motif-negative peptide, consisting of amino acids 1–20 of SEQ ID NO: 48) derived from a non-immunizing T cell clone, was apparent after vaccination. However, the magnitude of the specific proliferation in response to the motif-positive peptide was considerably lower than that induced by irradiated immunizing T cells (FIG. 8A). The proliferative response to the immunizing T cells correlated inversely with a decline in the frequency of circulating MBP-reactive T cells in the immunized patients (FIG. 8B).

The Generation of B Cell Lines Producing Specific Antibodies to the TCR Peptide Incorporating the Common CER3 Sequence from Immunized Patients We then examined whether immunization with irradiated T cells would elicit specific anti-idiotypic antibody responses in the patients. As the whole T cells expressed an array of surface molecules that could interfere with the detection of serum anti-idiotypic antibodies, the TCR peptide incorporating the common CDR3 sequence (motif-positive peptide) was used as the antigen for screening. The 20-mer TCR peptide derived from a non-immunizing MBP-reactive T cell clone (motif-negative peptide) was included in all experiments as a control. The CDR3 sequence of the control peptide was not detected in the immunizing T cell clones.

No specific antibody reactivity to either the TCR peptide or the original immunizing T cells could be detected using ELISA or flow cytometry, when tested with sera derived from the two patients (data not shown). To further verify whether anti-idiotypic antibodies were present in the vaccinated patients, we generated a panel of antibody-producing B cell lines from the post-vaccination blood specimens using a cell culture-based technique combining EBV transformation with limiting dilution (see Materials and Methods).

Figure 9:
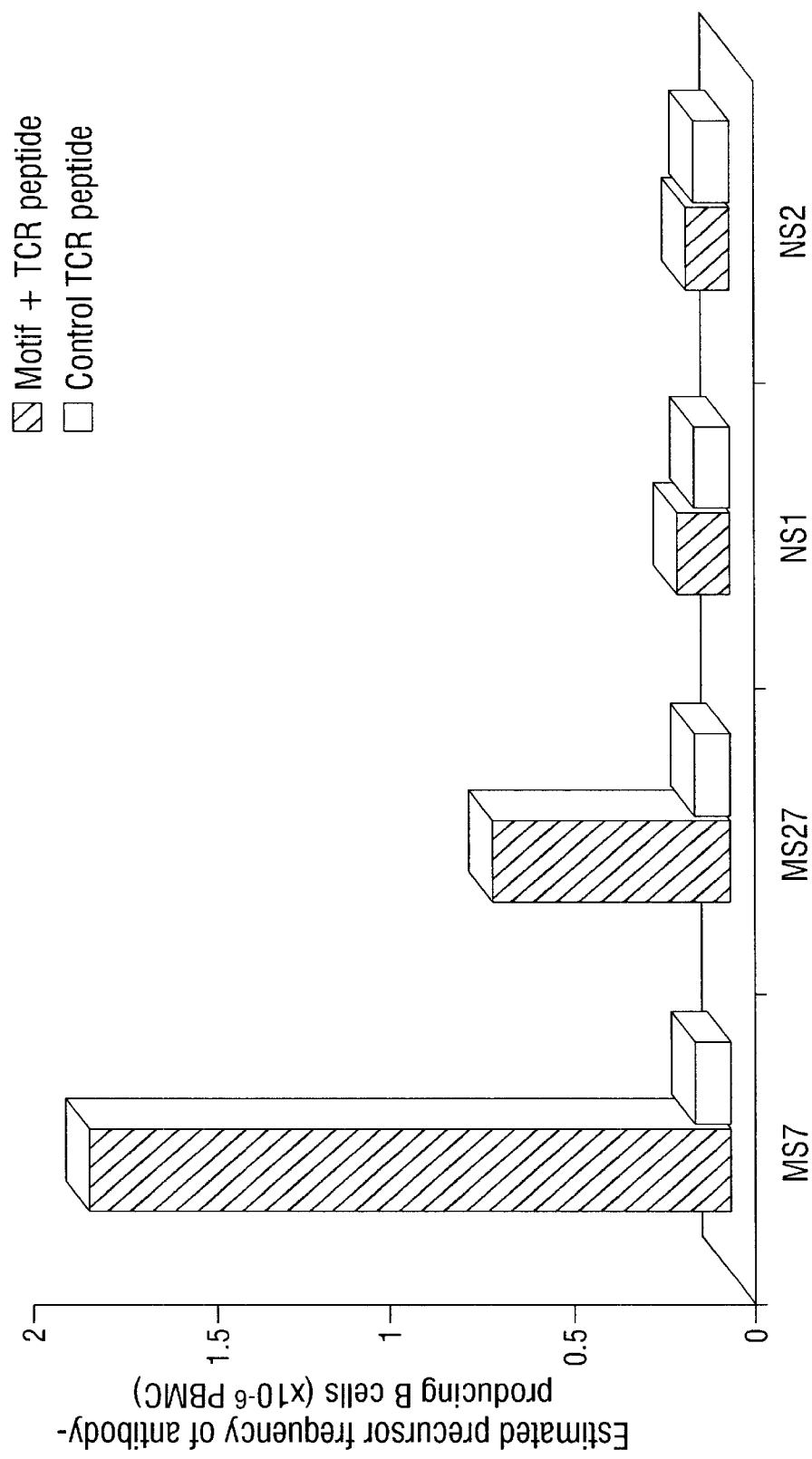
FIG. 9 shows the estimated precursor frequency of B cells producing anti-idiotypic antibodies to the TCR peptide in PBMCs of immunized patients. PBMCs were obtained from two immunized MS patients and two randomly selected healthy individuals that were not immunized. Cells were cultured in the presence of supernatants derived from an EBV-producing cell line and Cyclosporin A (Sandoz, Basel, Switzerland). All growth-positive wells were screened for the presence of antibodies reactive to the motif-positive TCR peptide and the control TCR peptide in ELISA. The precursor frequency of B cells producing anti-idiotypic antibodies to the TCR peptide was estimated by dividing the number of positive wells by the total number of PBMC initially plated.

As pre-vaccination PBMC were not available for the experiments, cells obtained from two randomly selected healthy individuals were used as control subjects and analyzed under the same experimental condition. Supernatants of the resulting B cell lines (92 cell lines from each patient/individual) were tested for the presence of antibodies to the motif-positive TCR peptide and the control TCR peptide, respectively, in ELISA. Antibodies were defined as anti-idiotypic when they exhibited specific reactivity to the motif-positive TCR peptide but not the control TCR peptide. As shown in FIG. 9, B cells producing specific anti-idiotypic antibodies occurred at the precursor frequency of $1.75 \times 10^{-6}$ in patients MS7 & and MS27, respectively, as compared to two non-immunized control subjects. In contrast, no specific antibody reactivity to the control peptide was detected in the same supernatants. The results suggest that the high frequency of B cells producing anti-idiotypic antibodies was associated with T cell vaccination.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

All references listed herein, insofar as they are necessary to describe and/or enable the present claims are hereby incorporated by reference.

Hjelmeland, J. M. and Chrambach, A. (1984) "Solubilization of functional membrane proteins" *Meth. Enzymol.* 104:305–318

Medaer, R. P., Stinissen, L., Raus, J. and Zhang, J. (1995) "Depletion of myelin basic protein-reactive T cells by T cell vaccination: A pilot clinical trial in multiple sclerosis", *Lancet* 346:807–808.

Vandevyver, C., Mertens, N., van de Elson, P., Medaer, R., Raus, J., and Zhang, J. (1995) "Clonal expansion of myelin basic protein-reactive T cells in patients with multiple sclerosis: restricted T cell receptor V gene rearrangements and DCR3 sequence." *Eur. J. Immunol.* 25:958–968.

Zhang, J., Lambrechts, J., Heyligen, H., Vandenbark, A., and Raus, J. (1989) "Human B cell lines secreting IgM antibody specific for myelin basic protein." *J. Neuroimmunol.* 23:249.

Zhang, J., Chin, Y., Henderikx, P., Medaer, R.,.Chou, C. H., and Raus, J. (1991) "Antibodies to myelin basic protein and measles virus in multiple sclerosis: precursor frequency analysis of the antibody producing B cells." *Autoimm.* 11:27.

Zhang, J., Medaer, R., Hashim, G., Ying, C. van den Berg-Loonen, E., and Raus, J. (1992) "Myelin basic protein-specific T lymphocytes in multiple sclerosis and controls: precursor frequency, fine specificity, and cytotoxicity." *Ann. Neurol.* 32:330.

Zhang, J., Medaer, R., Stinissen, P., Hafler, D. A., and Raus, J. (1993) "MHC restricted depletion of human myelin basic protein reactive T cells by T cell vaccination." *Science* 261:1451–1454

Zhang, Y. C. Q., Kozovska, M., Aebischer, I., Li, S., Boehme, S., Crowe, P., Rivera, V. M., and Zhang, J. (1998) "Restricted TCR Vα gene rearrangement in T cells recognizing an immunodominant peptide of myelin basic protein in DR2 patients with multiple sclerosis." *Int. Immunol.* 10:991

What is claimed is:

1. A peptide of from 8 to approximately 32 amino acids which comprises the sequence of SEQ ID NO:3.

2. The peptide of claim 1 which comprises amino acids 2–21 of SEQ ID NO:32.

3. The peptide of claim 1 which consists of amino acids 2–21 of SEQ ID NO:32.

4. The peptide of claim 1 which consists of the sequence of SEQ ID NO:3.

* * * * *

UNITED STATES PATENT AND TRADEMARK OFFICE
CERTIFICATE OF CORRECTION

PATENT NO. : 6,541,608 B1
DATED : April 1, 2003
INVENTOR(S) : Jingwu Z. Zhang

It is certified that error appears in the above-identified patent and that said Letters Patent is hereby corrected as shown below:

Column 1,
Line 12, after "Background" insert -- of --.

Column 2,
Line 27, after "SEQ ID NO:" insert -- 1 --;
Line 37, replace "oligonucleotide is" with -- oligonucleotide of --
Line 42, replace "15 and 30" with -- 15 to 30 --; and
Line 60, replace "nucleotide" with -- nucleotides --.

Column 3,
Line 5, replace "digoxingenin" with -- digoxigenin --;
Line 19, replace "15 and 30" with -- 15 to 30 --;

Column 4,
Line 17, after "specimens" delete -- were --.

Column 5,
Line 30, replace "a" with -- an --;
Line 49, replace "respectively7" with -- respectively --.

Column 6,
Line 11, replace "again with -- agent --;
Line 30, replace "Lue" with -- Leu --.

Column 7,
Line 6, replace "15 and 30" with -- 15 to 30 --;
Line 14, after "SEQ ID NO:" insert -- 1 --.

Column 9,
Line 48, replace "a oligonucleotide" with -- an oligonucleotide --; and
Line 61, replace "digoxingenin" with -- digoxigenin --.

Column 10,
Line 10, delete "at";
Line 12, delete "an";
Line 29, replace "thereto" with -- thereto. --;
Line 36, replace "LGPAGLTY" with -- LGRAGLTY --; and
Line 42, replace "digoxingenin" with -- digoxigenin --.

UNITED STATES PATENT AND TRADEMARK OFFICE
CERTIFICATE OF CORRECTION

PATENT NO.   : 6,541,608 B1
DATED        : April 1, 2003
INVENTOR(S)  : Jingwu Z. Zhang It is certified that error appears in the above-identified patent and that said Letters Patent is hereby corrected as shown below:

Column 11,
Line 7, replace "Pat. No." with -- Pat. Nos. --.

Column 12,
Line 20, replace "above" with -- above. --.

Column 13,
Lines 11 and 19, replace "Table 1." with -- Table 1 --.

Column 14,
Line 4, replace "digoxingenin" with -- digoxigenin --;
Lines 6 and 13, replace "Table 2." with -- Table 2 --; and
Line 9, replace "primer" with -- primers --.

Column 22,
Line 33, replace "Myclin-Reactive" with -- Myelin Reactive --.

Column 23,
Line 49, replace "ere then blocked" with -- were then blocked --; and
Line 56, replace "lgG/1 g" with -- lgG/lgM --.

Column 24,
Line 8, replace "power" with -- powder --.

Signed and Sealed this

Twenty-seventh Day of July, 2004

JON W. DUDAS
*Acting Director of the United States Patent and Trademark Office*

SEQUENCE LISTING

<160> NUMBER OF SEQ ID NOS: 77

<210> SEQ ID NO 1
<211> LENGTH: 24
<212> TYPE: DNA
<213> ORGANISM: SYNTHETIC

<400> SEQUENCE: 1
ctagggcggg cgggactcac ctac                                             24

<210> SEQ ID NO 2
<211> LENGTH: 400
<212> TYPE: DNA
<213> ORGANISM: Homo sapiens

<400> SEQUENCE: 2
catgtctccg ataacccaga ggatttcccg ctcaggctgc tgtcggctgc tccctcccag      60
acatctgtgt acttctgtgc cagcagccta gggcgggcgg gactcaccta cgagcagtac    120
ttcgggccgg gcaccaggct cacggtcaca gaggacctga aaaacgtgtt cccacccgag    180
gtcgctgtgt tgagccatc agaagcagag atctcccaca cccaaaaggc cacactggta    240
tgcctggcca caggcttcta ccccgaccac gtggagctga gctggtgggt gaatgggaag    300
gaggtgcaca gtgggtcag cacagacccg cagcccctca aggagcagcc cgccctcaat    360
gactccagat actgcctgag cagccgcctg agggtctcgg                           400

<210> SEQ ID NO 3
<211> LENGTH: 8
<212> TYPE: PRT
<213> ORGANISM: Homo sapiens

<400> SEQUENCE: 3

Leu Gly Arg Ala Gly Leu Thr Tyr
 1               5

<210> SEQ ID NO 4
<211> LENGTH: 30
<212> TYPE: PRT
<213> ORGANISM: Homo sapiens

<400> SEQUENCE: 4

Tyr Phe Cys Ala Leu Ser Arg Gly Gly Ser Asn Tyr Lys Leu Thr Phe
 1               5                  10                  15

Gly Lys Gly Thr Leu Leu Thr Val Asn Pro Asn Ile Gln Asn
            20                  25                  30

<210> SEQ ID NO 5
<211> LENGTH: 90
<212> TYPE: DNA
<213> ORGANISM: Homo sapiens

<400> SEQUENCE: 5
tacttctgtg ctctgagtag gggaggtagc aactataaac tgacatttgg aaaaggaact     60
ctcttaaccg tgaatccaaa tatccagaac                                      90

<210> SEQ ID NO 6
<211> LENGTH: 30
<212> TYPE: PRT
<213> ORGANISM: Homo sapiens

```
<400> SEQUENCE: 6

Tyr Tyr Cys Ala Leu Lys Arg Asn Phe Gly Asn Glu Lys Leu Thr Phe
 1               5                  10                  15
Gly Thr Gly Thr Arg Leu Thr Ile Ile Pro Asn Ile Gln Asn
            20                  25                  30

<210> SEQ ID NO 7
<211> LENGTH: 90
<212> TYPE: DNA
<213> ORGANISM: Homo sapiens

<400> SEQUENCE: 7
tattactgtg ctctaaaaag aaactttgga aatgagaaat taacctttgg gactggaaca      60
agactcacca tcatacccaa tatccagaac                                       90

<210> SEQ ID NO 8
<211> LENGTH: 30
<212> TYPE: PRT
<213> ORGANISM: Homo sapiens

<400> SEQUENCE: 8

Tyr Phe Cys Ala Ala Ser Pro Gly Gly Ser Asn Tyr Lys Leu Thr Phe
 1               5                  10                  15
Gly Lys Gly Thr Leu Leu Thr Val Asn Pro Asn Ile Gln Asn
            20                  25                  30

<210> SEQ ID NO 9
<211> LENGTH: 90
<212> TYPE: DNA
<213> ORGANISM: Homo sapiens

<400> SEQUENCE: 9
tacttctgtg cagcaagccc cggaggtagc aactataaac tgacatttgg aaaggaact       60 ctcttaaccg tgaatccaaa tatccagaac                                       90

<210> SEQ ID NO 10
<211> LENGTH: 30
<212> TYPE: PRT
<213> ORGANISM: Homo sapiens

<400> SEQUENCE: 10

Tyr Phe Cys Ala Ala Met Gly Asp Phe Gly Asn Glu Lys Leu Thr Phe
 1               5                  10                  15
Gly Thr Gly Thr Arg Leu Thr Ile Ile Pro Asn Ile Gln Asn
            20                  25                  30

<210> SEQ ID NO 11
<211> LENGTH: 90
<212> TYPE: DNA
<213> ORGANISM: Homo sapiens

<400> SEQUENCE: 11
tacttctgtg cagcaatggg ggactttgga aatgagaaat taacctttgg gactggaaca      60
agactcacca tcatacccaa tatccagaac                                       90

<210> SEQ ID NO 12
<211> LENGTH: 30
<212> TYPE: PRT
<213> ORGANISM: Homo sapiens

<400> SEQUENCE: 12
```

```
Tyr Phe Cys Ala Ala Met Gly Asp Phe Gly Asn Glu Lys Leu Thr Phe
 1               5                  10                  15
Gly Thr Gly Thr Arg Leu Thr Ile Ile Pro Asn Ile Gln Asn
            20                  25                  30
```

<210> SEQ ID NO 13
<211> LENGTH: 90
<212> TYPE: DNA
<213> ORGANISM: Homo sapiens

<400> SEQUENCE: 13

```
tacttctgtg cagcaatggg ggactttgga aatgagaaat taacctttgg gactggaaca      60
agactcacca tcatacccaa tatccagaac                                       90
```

<210> SEQ ID NO 14
<211> LENGTH: 30
<212> TYPE: PRT
<213> ORGANISM: Homo sapiens

<400> SEQUENCE: 14

```
Tyr Phe Cys Ala Ala Met Gly Asp Phe Gly Asn Glu Lys Leu Thr Phe
 1               5                  10                  15
Gly Thr Gly Thr Arg Leu Thr Ile Ile Pro Asn Ile Gln Asn
            20                  25                  30
```

<210> SEQ ID NO 15
<211> LENGTH: 90
<212> TYPE: DNA
<213> ORGANISM: Homo sapiens

<400> SEQUENCE: 15

```
tacttctgtg cagcaatggg ggactttgga aatgagaaat taacctttgg gactggaaca      60
agactcacca tcatacccaa tatccagaac                                       90
```

<210> SEQ ID NO 16
<211> LENGTH: 32
<212> TYPE: PRT
<213> ORGANISM: Homo sapiens

<400> SEQUENCE: 16

```
Tyr Phe Cys Ala Leu Ser Val Ala Gly Gly Thr Ser Tyr Gly Lys Leu
 1               5                  10                  15
Thr Phe Gly Gln Gly Thr Ile Leu Thr Val His Pro Asn Ile Gln Asn
            20                  25                  30
```

<210> SEQ ID NO 17
<211> LENGTH: 96
<212> TYPE: DNA
<213> ORGANISM: Homo sapiens

<400> SEQUENCE: 17

```
tacttctgtg ctctgagcgt tgctggtggt actagctatg gaaagctgac atttggacaa      60
gggaccatct tgactgtcca tccaaatatc cagaac                                96
```

<210> SEQ ID NO 18
<211> LENGTH: 33
<212> TYPE: PRT
<213> ORGANISM: Homo sapiens

<400> SEQUENCE: 18

-continued

```
Tyr Tyr Cys Leu Val Gly Asp Ala Val Arg Pro Gly Gly Gly Asn Lys
 1               5                  10                  15

Leu Thr Phe Gly Thr Gly Thr Gln Leu Lys Val Glu Leu Asn Ile Gln
                20                  25                  30

Asn

<210> SEQ ID NO 19
<211> LENGTH: 99
<212> TYPE: DNA
<213> ORGANISM: Homo sapiens

<400> SEQUENCE: 19
tactactgcc tcgtgggtga cgccgtgagg ccgggaggag gaaacaaact cacctttggg    60
acaggcactc agctaaaagt ggaactcaat atccagaac                          99

<210> SEQ ID NO 20
<211> LENGTH: 33
<212> TYPE: PRT
<213> ORGANISM: Homo sapiens

<400> SEQUENCE: 20

Tyr Tyr Cys Leu Val Gly Asp Ala Val Arg Pro Gly Gly Gly Asn Lys
 1               5                  10                  15

Leu Thr Phe Gly Thr Gly Thr Gln Leu Lys Val Glu Leu Asn Ile Gln
                20                  25                  30

Asn

<210> SEQ ID NO 21
<211> LENGTH: 99
<212> TYPE: DNA
<213> ORGANISM: Homo sapiens

<400> SEQUENCE: 21
tactactgcc tcgtgggtga cgccgtgagg ccgggaggag gaaacaaact cacctttggg    60
acaggcactc agctaaaagt ggaactcaat atccagaac                          99

<210> SEQ ID NO 22
<211> LENGTH: 29
<212> TYPE: PRT
<213> ORGANISM: Homo sapiens

<400> SEQUENCE: 22

Tyr Phe Cys Ala Thr Asp Ala Gly Gly Thr Tyr Lys Tyr Ile Phe Gly
 1               5                  10                  15

Thr Gly Thr Arg Leu Lys Val Leu Ala Asn Ile Gln Asn
                20                  25

<210> SEQ ID NO 23
<211> LENGTH: 87
<212> TYPE: DNA
<213> ORGANISM: Homo sapiens

<400> SEQUENCE: 23
tacttctgtg ctacggacgc aggaggaacc tacaaataca tctttggaac aggcaccagg    60
ctgaaggttt tagcaaatat ccagaac                                       87

<210> SEQ ID NO 24
<211> LENGTH: 27
<212> TYPE: PRT
<213> ORGANISM: Homo sapiens
```

<400> SEQUENCE: 24

Tyr Tyr Cys Leu Val Gly Asp Ile Asp Asp Met Arg Phe Gly Ala Gly
1               5                   10                  15

Thr Arg Leu Thr Val Lys Pro Asn Ile Gln Asn
            20                  25

<210> SEQ ID NO 25
<211> LENGTH: 81
<212> TYPE: DNA
<213> ORGANISM: Homo sapiens

<400> SEQUENCE: 25
tactactgcc tcgtgggtga catcgatgac atgcgctttg agcagggac cagactgaca      60 gtaaaaccaa atatccagaa c                                              81

<210> SEQ ID NO 26
<211> LENGTH: 28
<212> TYPE: PRT
<213> ORGANISM: Homo sapiens

<400> SEQUENCE: 26

Tyr Phe Cys Ala Thr Ser Val Asn Thr Asp Lys Leu Ile Phe Gly Thr
1               5                   10                  15

Gly Thr Arg Leu Gln Val Phe Pro Asn Ile Gln Asn
            20                  25

<210> SEQ ID NO 27
<211> LENGTH: 84
<212> TYPE: DNA
<213> ORGANISM: Homo sapiens

<400> SEQUENCE: 27
tacttctgtg ctacatcggt taacaccgac aagctcatct ttgggactgg gaccagatta    60
caagtctttc caaatatcca gaac                                           84

<210> SEQ ID NO 28
<211> LENGTH: 35
<212> TYPE: PRT
<213> ORGANISM: Homo sapiens

<400> SEQUENCE: 28

Tyr Phe Cys Ala Ser Ser Gln Asp Arg Phe Trp Gly Gly Thr Val Asn
1               5                   10                  15

Thr Glu Ala Phe Phe Gly Gln Gly Thr Arg Leu Thr Val Val Glu Asp
            20                  25                  30

Leu Asn Lys
        35

<210> SEQ ID NO 29
<211> LENGTH: 105
<212> TYPE: DNA
<213> ORGANISM: Homo sapiens

<400> SEQUENCE: 29
tatttctgtg ccagcagcca agatcgtttt tggggggggga cggtgaacac tgaagctttc    60
tttggacaag gcaccagact cacagttgta gaggacctga acaag                    105

<210> SEQ ID NO 30
<211> LENGTH: 28

```
<212> TYPE: PRT
<213> ORGANISM: Homo sapiens

<400> SEQUENCE: 30

Tyr Phe Cys Ala Ser Ser Ala Met Gly Glu Thr Gln Tyr Phe Gly Pro
 1               5                  10                  15

Gly Thr Arg Leu Leu Val Leu Glu Asp Leu Lys Asn
             20                  25

<210> SEQ ID NO 31
<211> LENGTH: 84
<212> TYPE: DNA
<213> ORGANISM: Homo sapiens

<400> SEQUENCE: 31
tatttctgtg ccagcagcgc tatgggagag acccagtact tcgggccagg cacgcggctc    60
ctggtgctcg aggacctgaa aaac                                          84

<210> SEQ ID NO 32
<211> LENGTH: 32
<212> TYPE: PRT
<213> ORGANISM: Homo sapiens

<400> SEQUENCE: 32

Tyr Phe Cys Ala Ser Ser Leu Gly Arg Ala Gly Leu Thr Tyr Glu Gln
 1               5                  10                  15

Tyr Phe Gly Pro Gly Thr Arg Leu Thr Val Thr Glu Asp Leu Lys Asn
             20                  25                  30

<210> SEQ ID NO 33
<211> LENGTH: 96
<212> TYPE: DNA
<213> ORGANISM: Homo sapiens

<400> SEQUENCE: 33
tacttctgtg ccagcagcct agggcgggcg ggactcacct acgagcagta cttcgggccg    60
ggcaccaggc tcacggtcac agaggacctg aaaaac                             96

<210> SEQ ID NO 34
<211> LENGTH: 32
<212> TYPE: PRT
<213> ORGANISM: Homo sapiens

<400> SEQUENCE: 34

Tyr Phe Cys Ala Ser Ser Leu Gly Arg Ala Gly Leu Thr Tyr Glu Gln
 1               5                  10                  15

Tyr Phe Gly Pro Gly Thr Arg Leu Thr Val Thr Glu Asp Leu Lys Asn
             20                  25                  30

<210> SEQ ID NO 35
<211> LENGTH: 96
<212> TYPE: DNA
<213> ORGANISM: Homo sapiens

<400> SEQUENCE: 35
tacttctgtg ccagcagcct agggcgggcg ggactcacct acgagcagta cttcgggccg    60
ggcaccaggc tcacggtcac agaggacctg aaaaac                             96

<210> SEQ ID NO 36
<211> LENGTH: 31
<212> TYPE: PRT
```

<213> ORGANISM: Homo sapiens

<400> SEQUENCE: 36

Phe Cys Ala Ser Ser Leu Gly Arg Ala Gly Leu Thr Tyr Glu Gln Tyr
 1               5                  10                  15

Phe Gly Pro Gly Thr Arg Leu Thr Val Thr Glu Asp Leu Lys Asn
            20                  25                  30

<210> SEQ ID NO 37
<211> LENGTH: 96
<212> TYPE: DNA
<213> ORGANISM: Homo sapiens

<400> SEQUENCE: 37
tacttctgtg ccagcagcct agggcgggcg ggactcacct acgagcagta cttcgggccg    60
ggcaccaggc tcacggtcac agaggacctg aaaaac    96

<210> SEQ ID NO 38
<211> LENGTH: 32
<212> TYPE: PRT
<213> ORGANISM: Homo sapiens

<400> SEQUENCE: 38

Tyr Phe Cys Ala Ser Ser Leu Gly Arg Ala Gly Leu Thr Tyr Glu Gln
 1               5                  10                  15

Tyr Phe Gly Pro Gly Thr Arg Leu Thr Val Thr Glu Asp Leu Lys Asn
            20                  25                  30

<210> SEQ ID NO 39
<211> LENGTH: 96
<212> TYPE: DNA
<213> ORGANISM: Homo sapiens

<400> SEQUENCE: 39
tacttctgtg ccagcagcct agggcgggcg ggactcacct acgagcagta cttcgggccg    60
ggcaccaggc tcacggtcac agaggacctg aaaaac    96

<210> SEQ ID NO 40
<211> LENGTH: 29
<212> TYPE: PRT
<213> ORGANISM: Homo sapiens

<400> SEQUENCE: 40

Tyr Phe Cys Ala Ser Ser Pro Thr Val Asn Tyr Gly Tyr Thr Phe Gly
 1               5                  10                  15

Ser Gly Thr Arg Leu Thr Val Val Glu Asp Leu Asn Lys
            20                  25

<210> SEQ ID NO 41
<211> LENGTH: 87
<212> TYPE: DNA
<213> ORGANISM: Homo sapiens

<400> SEQUENCE: 41
tatttctgtg ccagcagccc gacagttaac tatggctaca ccttcggttc ggggaccagg    60
ttaaccgttg tagaggacct gaacaag    87

<210> SEQ ID NO 42
<211> LENGTH: 32
<212> TYPE: PRT
<213> ORGANISM: Homo sapiens

```
<400> SEQUENCE: 42

Tyr Phe Cys Ala Ser Ser Tyr Ser Ile Arg Gly Gln Gly Asn Glu Gln
 1               5                  10                  15

Tyr Phe Gly Pro Gly Thr Arg Leu Thr Val Thr Glu Asp Leu Lys Asn
                20                  25                  30

<210> SEQ ID NO 43
<211> LENGTH: 96
<212> TYPE: DNA
<213> ORGANISM: Homo sapiens

<400> SEQUENCE: 43
tacttctgtg ccagcagtta ctcgattagg ggacagggta acgagcagta cttcgggccg     60
ggcaccaggc tcacggtcac agaggacctg aaaaac                               96

<210> SEQ ID NO 44
<211> LENGTH: 32
<212> TYPE: PRT
<213> ORGANISM: Homo sapiens

<400> SEQUENCE: 44

Tyr Phe Cys Ala Ser Ser Tyr Ser Ile Arg Gly Gln Gly Asn Glu Gln
 1               5                  10                  15

Tyr Phe Arg Pro Gly Thr Arg Leu Thr Val Thr Glu Asp Leu Lys Asn
                20                  25                  30

<210> SEQ ID NO 45
<211> LENGTH: 96
<212> TYPE: DNA
<213> ORGANISM: Homo sapiens

<400> SEQUENCE: 45
tacttctgtg ccagcagtta ctcgattagg ggacagggta acgagcagta cttccggccg     60
ggcaccaggc tcacggtcac agaggacctg aaaaac                               96

<210> SEQ ID NO 46
<211> LENGTH: 29
<212> TYPE: PRT
<213> ORGANISM: Homo sapiens

<400> SEQUENCE: 46

Tyr Leu Cys Ala Ser Ser Gln Asp Arg Val Ala Pro Gln Tyr Phe Gly
 1               5                  10                  15

Pro Gly Thr Arg Leu Leu Val Leu Glu Asp Leu Lys Asn
                20                  25

<210> SEQ ID NO 47
<211> LENGTH: 87
<212> TYPE: DNA
<213> ORGANISM: Homo sapiens

<400> SEQUENCE: 47
tatctctgtg ccagcagcca agatcgggtt gcgccacagt acttcgggcc aggcacgcgg     60
ctcctggtgc tcgaggacct gaaaaac                                         87

<210> SEQ ID NO 48
<211> LENGTH: 31
<212> TYPE: PRT
<213> ORGANISM: Homo sapiens
```

<400> SEQUENCE: 48

Tyr Leu Cys Ala Ser Ser Thr Arg Gln Gly Pro Gln Glu Thr Gln Tyr
1               5                   10                  15
Phe Gly Pro Gly Thr Arg Leu Leu Val Leu Glu Asp Leu Lys Asn
            20                  25                  30

<210> SEQ ID NO 49
<211> LENGTH: 93
<212> TYPE: DNA
<213> ORGANISM: Homo sapiens

<400> SEQUENCE: 49
tatctctgtg ccagtagtac ccggcaagga cctcaagaga cccagtactt cgggccaggc    60
acgcggctcc tggtgctcga ggacctgaaa aac                                 93

<210> SEQ ID NO 50
<211> LENGTH: 30
<212> TYPE: PRT
<213> ORGANISM: Homo sapiens

<400> SEQUENCE: 50

Tyr Leu Cys Ala Ser Ser Leu Gly Gln Gly Ala Tyr Glu Gln Tyr Phe
1               5                   10                  15
Gly Pro Gly Thr Arg Leu Thr Val Thr Glu Asp Leu Lys Asn
            20                  25                  30

<210> SEQ ID NO 51
<211> LENGTH: 90
<212> TYPE: DNA
<213> ORGANISM: Homo sapiens

<400> SEQUENCE: 51
tatctctgtg ccagcagctt aggacagggg gcttacgagc agtacttcgg gccgggcacc    60
aggctcacgg tcacagagga cctgaaaaac                                     90

<210> SEQ ID NO 52
<211> LENGTH: 30
<212> TYPE: PRT
<213> ORGANISM: Homo sapiens

<400> SEQUENCE: 52

Tyr Leu Cys Ala Ser Ser Leu Gly Gln Gly Ala Tyr Glu Gln Tyr Phe
1               5                   10                  15
Gly Pro Gly Thr Arg Leu Thr Val Thr Glu Asp Leu Lys Asn
            20                  25                  30

<210> SEQ ID NO 53
<211> LENGTH: 90
<212> TYPE: DNA
<213> ORGANISM: Homo sapiens

<400> SEQUENCE: 53
tatctctgtg ccagcagctt aggacagggg gcttacgagc agtacttcgg gccgggcacc    60
aggctcacgg tcacagagga cctgaaaaac                                     90

<210> SEQ ID NO 54
<211> LENGTH: 30
<212> TYPE: PRT
<213> ORGANISM: Homo sapiens

<400> SEQUENCE: 54

Tyr Leu Cys Ala Ser Ser Leu Gly Gln Gly Ala Tyr Glu Gln Tyr Phe
 1               5                  10                  15

Gly Pro Gly Thr Arg Leu Thr Val Thr Glu Asp Leu Lys Asn
            20                  25                  30

<210> SEQ ID NO 55
<211> LENGTH: 90
<212> TYPE: DNA
<213> ORGANISM: Homo sapiens

<400> SEQUENCE: 55
tatctctgtg ccagcagctt aggacagggg gcttacgagc agtacttcgg gccgggcacc     60
aggctcacgg tcacagagga cctgaaaaac                                     90

<210> SEQ ID NO 56
<211> LENGTH: 29
<212> TYPE: PRT
<213> ORGANISM: Homo sapiens

<400> SEQUENCE: 56

Tyr Phe Cys Ala Ser Ser Leu Gln Val Tyr Ser Pro Leu His Phe Gly
 1               5                  10                  15

Asn Gly Thr Arg Leu Thr Val Thr Glu Asp Leu Asn Lys
            20                  25

<210> SEQ ID NO 57
<211> LENGTH: 87
<212> TYPE: DNA
<213> ORGANISM: Homo sapiens

<400> SEQUENCE: 57
tacttctgtg ccagcagttt acaagtgtat tcacccctcc actttgggaa cgggaccagg     60
ctcactgtga cagaggacct gaacaag                                        87

<210> SEQ ID NO 58
<211> LENGTH: 31
<212> TYPE: PRT
<213> ORGANISM: Homo sapiens

<400> SEQUENCE: 58

Tyr Phe Cys Ala Ile Ser Glu Ser Ile Gly Thr Gly Thr Glu Ala Phe
 1               5                  10                  15

Phe Gly Gln Gly Thr Arg Leu Thr Val Val Glu Asp Leu Asn Lys
            20                  25                  30

<210> SEQ ID NO 59
<211> LENGTH: 93
<212> TYPE: DNA
<213> ORGANISM: Homo sapiens

<400> SEQUENCE: 59
tacttctgtg ccatcagtga gtcgattggt acgggaactg aagctttctt tggacaaggc     60
accagactca cagttgtaga ggacctgaac aag                                 93

<210> SEQ ID NO 60
<211> LENGTH: 31
<212> TYPE: PRT
<213> ORGANISM: Homo sapiens

<400> SEQUENCE: 60

-continued

Tyr Phe Cys Ala Ile Ser Glu Ser Ile Gly Thr Gly Thr Glu Ala Phe
1               5                   10                  15

Phe Gly Gln Gly Thr Arg Leu Thr Val Val Glu Asp Leu Asn Lys
                20                  25                  30

<210> SEQ ID NO 61
<211> LENGTH: 93
<212> TYPE: DNA
<213> ORGANISM: Homo sapiens

<400> SEQUENCE: 61
tacttctgtg ccatcagtga gtcgattggt acgggaactg aagctttctt tggacaaggc      60
accagactca cagttgtaga ggacctgaac aag                                   93

<210> SEQ ID NO 62
<211> LENGTH: 28
<212> TYPE: PRT
<213> ORGANISM: Homo sapiens

<400> SEQUENCE: 62

Tyr Leu Cys Ala Ser Arg Asp Arg Ser Tyr Glu Gln Tyr Phe Gly Pro
1               5                   10                  15

Gly Thr Arg Leu Thr Val Thr Glu Asp Leu Lys Asn
                20                  25

<210> SEQ ID NO 63
<211> LENGTH: 84
<212> TYPE: DNA
<213> ORGANISM: Homo sapiens

<400> SEQUENCE: 63
tacctctgtg ccagccggga caggtcctac gagcagtact cgggccgggg caccaggctc      60
acggtcacag aggacctgaa aaac                                             84

<210> SEQ ID NO 64
<211> LENGTH: 31
<212> TYPE: PRT
<213> ORGANISM: Homo sapiens

<400> SEQUENCE: 64

Tyr Phe Cys Ala Ile Ser Glu Gly Ser Ser Ser Gly Asn Thr Ile Tyr
1               5                   10                  15
Phe Gly Glu Gly Ser Trp Leu Thr Val Val Glu Asp Leu Asn Lys
                20                  25                  30

<210> SEQ ID NO 65
<211> LENGTH: 93
<212> TYPE: DNA
<213> ORGANISM: Homo sapiens

<400> SEQUENCE: 65
tacttctgtg ccatcagtga ggggtccagc tctggaaaca ccatatattt tggagaggga      60
agttggctca ctgttgtaga ggacctgaac aag                                   93

<210> SEQ ID NO 66
<211> LENGTH: 26
<212> TYPE: PRT
<213> ORGANISM: Homo sapiens

<400> SEQUENCE: 66

Phe Tyr Ile Cys Ser Ala Ile Asp Gly Tyr Thr Phe Gly Ser Gly Thr
1               5                   10                  15

-continued

Arg Leu Thr Val Val Glu Asp Leu Asn Lys
            20                  25

<210> SEQ ID NO 67
<211> LENGTH: 78
<212> TYPE: DNA
<213> ORGANISM: Homo sapiens

<400> SEQUENCE: 67
ttctacatct gcagtgctat agacggctac accttcggtt cggggaccag gttaaccgtt    60
gtagaggacc tgaacaag                                                  78

<210> SEQ ID NO 68
<211> LENGTH: 21
<212> TYPE: DNA
<213> ORGANISM: Homo sapiens

<400> SEQUENCE: 68
agcagccaag atcgtttttg g                                              21

<210> SEQ ID NO 69
<211> LENGTH: 24
<212> TYPE: DNA
<213> ORGANISM: Homo sapiens

<400> SEQUENCE: 69
ctagggcggg cgggactcac ctac                                           24

<210> SEQ ID NO 70
<211> LENGTH: 24
<212> TYPE: DNA
<213> ORGANISM: Homo sapiens

<400> SEQUENCE: 70
ctagggcggg cgggactcac ctac                                           24

<210> SEQ ID NO 71
<211> LENGTH: 24
<212> TYPE: DNA
<213> ORGANISM: Homo sapiens

<400> SEQUENCE: 71
tactcgatta ggggacaggg taac                                           24

<210> SEQ ID NO 72
<211> LENGTH: 18
<212> TYPE: DNA
<213> ORGANISM: Homo sapiens

<400> SEQUENCE: 72
caagatcggg ttgcgcca                                                  18

<210> SEQ ID NO 73
<211> LENGTH: 24
<212> TYPE: DNA
<213> ORGANISM: Homo sapiens

<400> SEQUENCE: 73
acccggcaag gacctcaaga gacc                                           24

<210> SEQ ID NO 74
<211> LENGTH: 18

```
<212> TYPE: DNA
<213> ORGANISM: Homo sapiens

<400> SEQUENCE: 74
agcttaggac aggggct                                                  18

<210> SEQ ID NO 75
<211> LENGTH: 18
<212> TYPE: DNA
<213> ORGANISM: Homo sapiens

<400> SEQUENCE: 75
gccagccggg acaggtcc                                                 18

<210> SEQ ID NO 76
<211> LENGTH: 18
<212> TYPE: DNA
<213> ORGANISM: Homo sapiens

<400> SEQUENCE: 76
gagtagattg gtacggga                                                 18

<210> SEQ ID NO 77
<211> LENGTH: 21
<212> TYPE: DNA
<213> ORGANISM: Homo sapiens

<400> SEQUENCE: 77
tacatctgaa gtgctataga c                                             21
```